United States Patent
Stebbings et al.

(10) Patent No.: US 7,078,582 B2
(45) Date of Patent: Jul. 18, 2006

(54) STRETCH REMOVABLE ADHESIVE ARTICLES AND METHODS

(75) Inventors: William L. Stebbings, Stillwater, MN (US); Kevin D. Landgrebe, Woodbury, MN (US); Dave J. Hastings, London (CA); Wayne K. Dunshee, Maplewood, MN (US); Albert I. Everaerts, Oakdale, MN (US); Zhiming Zhou, Woodbury, MN (US); Robert C. Bennett, Edina, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 09/934,450

(22) Filed: Aug. 21, 2001

(65) Prior Publication Data

US 2002/0193724 A1 Dec. 19, 2002

Related U.S. Application Data

(63) Continuation-in-part of application No. 09/764,540, filed on Jan. 17, 2001, now abandoned.

(51) Int. Cl.
*A61F 13/00* (2006.01)

(52) U.S. Cl. .............................. 602/57; 602/54; 602/58
(58) Field of Classification Search ............. 602/41–59; 604/304–308; 28/888, 889; 442/400, 151, 442/328, 341, 351
See application file for complete search history.

(56) References Cited

U.S. PATENT DOCUMENTS

| 2,736,721 A | 2/1956 | Dexter et al. |
| RE24,906 E | 12/1960 | Ulrich |

(Continued)

FOREIGN PATENT DOCUMENTS

| CN | 2282880 | 6/1998 |
| DE | 27 28 346 | 5/1978 |
| DE | 33 31 016 C2 | 10/1984 |
| DE | 195 31 696 | 8/1995 |
| DE | 196 49 636 | 6/1998 |

(Continued)

OTHER PUBLICATIONS

"ASTM Standard D 1876–95, Standard Test Method for Peel Resistance of Adhesives (T–Peel Test)," *Annual Book of ASTM Standards*, vol. 15.06, pp. 115–117 (1995).

"ASTM Standard D 5459–95, Standard Test Method for Machine Direction Elastic Recovery and Permanent Deformation and Stress Retention of Stretch Wrap Film," *Annual Book of ASTM Standards*, vol. 14.02, pp. 742–744 (1995).

"ASTM Standard D 3759/D 3759M–96, Standard Test Method for Tensile Strength and Elongation of Pressure–Sensitive Tapes," *Annual Book of ASTM Standards*, vol. 14.02, pp. 434–439 (1996).

(Continued)

*Primary Examiner*—Kim M. Lewis

(57) ABSTRACT

Pressure sensitive adhesive articles and methods, particularly stretch removable adhesive articles that are preferably for use in adhering to skin or like delicate surfaces. Preferably, stretch removability of the article occurs as a result of the selection of a stretch removable pressure sensitive adhesive. In one embodiment of the articles and methods, the adhesive and backing delaminate upon removal. In another embodiment of the articles and methods, the backing includes a predefined tab located in a central location of the backing.

78 Claims, 5 Drawing Sheets

U.S. PATENT DOCUMENTS

| | | |
|---|---|---|
| 3,232,291 A | 2/1966 | Parker |
| 3,565,985 A | 2/1971 | Schrenk et al. |
| 3,691,140 A | 9/1972 | Silver |
| 3,825,379 A | 7/1974 | Lohkamp et al. |
| 3,849,241 A | 11/1974 | Butin et al. |
| 3,885,559 A | 5/1975 | Economou |
| 3,900,625 A | 8/1975 | Chen |
| 4,024,312 A | 5/1977 | Korpman |
| 4,197,069 A | 4/1980 | Cloeren |
| 4,260,659 A | 4/1981 | Gobran |
| 4,379,806 A | 4/1983 | Korpman |
| 4,413,621 A | 11/1983 | McCracken et al. |
| 4,425,176 A | 1/1984 | Shibano et al. |
| 4,488,619 A | 12/1984 | O'Neill |
| 4,619,979 A | 10/1986 | Kotnour et al. |
| 4,636,442 A | 1/1987 | Beavers et al. |
| 4,770,320 A | 9/1988 | Miles et al. |
| 4,792,480 A | 12/1988 | Freund et al. |
| 4,801,514 A | 1/1989 | Will et al. |
| 4,833,179 A | 5/1989 | Young et al. |
| 4,837,062 A | 6/1989 | Dunshee et al. |
| 4,837,088 A | 6/1989 | Freedman |
| 4,843,134 A | 6/1989 | Kotnour et al. |
| 4,894,259 A | 1/1990 | Kuller |
| 4,906,421 A | 3/1990 | Plamthottam et al. |
| 4,908,278 A | 3/1990 | Bland et al. |
| 4,937,134 A | 6/1990 | Schrenk et al. |
| 5,047,196 A | 9/1991 | Zuckerberg et al. |
| 5,064,653 A | 11/1991 | Sessions et al. |
| 5,086,946 A | 2/1992 | Blackwell et al. |
| 5,176,952 A | 1/1993 | Joseph et al. |
| 5,209,971 A | 5/1993 | Babu et al. |
| 5,215,087 A | 6/1993 | Anderson et al. |
| 5,232,770 A | 8/1993 | Joseph |
| 5,238,733 A | 8/1993 | Joseph et al. |
| 5,244,523 A | 9/1993 | Tollini |
| 5,248,455 A | 9/1993 | Joseph et al. |
| 5,258,220 A | 11/1993 | Joseph |
| 5,310,402 A | 5/1994 | Rollband |
| 5,314,557 A | 5/1994 | Schwartz et al. |
| 5,336,209 A | 8/1994 | Porzilli |
| 5,336,552 A | 8/1994 | Strack et al. |
| 5,344,697 A | 9/1994 | Romanowski |
| 5,382,400 A | 1/1995 | Pike et al. |
| 5,389,324 A | 2/1995 | Lewis et al. |
| 5,399,219 A | 3/1995 | Roessler et al. |
| 5,427,842 A | 6/1995 | Bland et al. |
| 5,437,622 A | 8/1995 | Carion |
| 5,461,134 A | 10/1995 | Leir et al. |
| 5,462,708 A | 10/1995 | Swenson et al. |
| 5,491,012 A | 2/1996 | Lühmann et al. |
| 5,496,599 A | 3/1996 | Schwartz et al. |
| 5,498,463 A | 3/1996 | McDowall et al. |
| 5,507,464 A | 4/1996 | Hamerski et al. |
| 5,512,358 A | 4/1996 | Shawver et al. |
| 5,516,581 A | 5/1996 | Kreckel et al. |
| 5,518,144 A | 5/1996 | Samuelson et al. |
| 5,545,464 A | 8/1996 | Stokes |
| 5,589,122 A | 12/1996 | Leonard et al. |
| 5,613,942 A | 3/1997 | Lucast et al. |
| 5,626,931 A | 5/1997 | Lühmann |
| 5,629,079 A | 5/1997 | Battles et al. |
| 5,637,646 A | 6/1997 | Ellis |
| 5,660,922 A | 8/1997 | Herridge et al. |
| 5,672,402 A | 9/1997 | Kreckel et al. |
| 5,695,868 A | 12/1997 | McCormack |
| 5,772,623 A | 6/1998 | Conte |
| 5,798,159 A | 8/1998 | Callahan, Jr. et al. |
| 5,989,708 A | 11/1999 | Kreckel |
| 6,001,471 A | 12/1999 | Bries et al. |
| 6,043,408 A * | 3/2000 | Geng .................. 602/58 |
| 6,045,895 A | 4/2000 | Hyde et al. |
| 6,063,838 A | 5/2000 | Patnode et al. |
| 6,083,856 A | 7/2000 | Joseph et al. |
| 6,107,219 A | 8/2000 | Joseph et al. |
| 6,133,173 A | 10/2000 | Riedel et al. |
| 6,136,397 A | 10/2000 | Luhmann et al. |
| 6,171,985 B1 | 1/2001 | Joseph et al. |
| 6,231,962 B1 | 5/2001 | Bries et al. |
| 6,280,840 B1 | 8/2001 | Lühmann et al. |
| D454,956 S | 3/2002 | Visintainer |
| 6,544,639 B1 | 4/2003 | Lühmann et al. |

FOREIGN PATENT DOCUMENTS

| | | |
|---|---|---|
| DE | 197 08 366 A1 | 8/1998 |
| EP | 0 066 899 | 12/1982 |
| EP | 0 186 154 | 7/1986 |
| EP | 0 066 899 B1 | 3/1988 |
| EP | 0 186 154 B1 | 7/1989 |
| EP | 0 788 784 B1 | 1/1993 |
| EP | 0 699 121 A1 | 8/1995 |
| EP | 0 747 027 | 12/1996 |
| EP | 0 788 784 | 8/1997 |
| EP | 0 845 517 A2 A3 | 6/1998 |
| EP | 0 669 121 B1 | 6/1999 |
| EP | 0 922 739 A1 | 6/1999 |
| EP | 0 957 146 A1 | 11/1999 |
| EP | 0 985 391 A2 | 3/2000 |
| EP | 0 987 309 A2 | 3/2000 |
| EP | 0 997 512 A2 | 5/2000 |
| EP | 0 788 784 B2 | 10/2000 |
| EP | 0 845 517 B1 | 8/2001 |
| FR | 2 686 018 | 7/1993 |
| FR | 2 711 056 | 4/1995 |
| GB | 2 131 299 A | 6/1984 |
| GB | 2 157 955 A | 11/1985 |
| GB | 2 286 762 A | 8/1995 |
| TW | 267938 | 1/1996 |
| WO | WO 95/17303 | 6/1995 |
| WO | WO 96/07522 | 3/1996 |
| WO | WO 96/08367 | 3/1996 |
| WO | WO 96/08369 | 3/1996 |
| WO | WO 96/25469 | 8/1996 |
| WO | WO 97/07760 | 3/1997 |
| WO | WO 97/23577 | 7/1997 |
| WO | WO 97/28771 | 8/1997 |
| WO | WO 97/43991 | 11/1997 |
| WO | WO 98/17216 | 4/1998 |
| WO | WO 02/072162 A2 | 9/2002 |
| WO | WO 02/089719 A1 | 11/2002 |

"ASTM Standard D 882–97, Standard Test Method for Tensile Properties of Thin Plastic Sheeting," *Annual Book of ASTM Standards,* vol. 14.02, pp. 165–173 (1997).

Lucast, Donald H., "Adhesive Considerations for Developing Stick–to–Skin Products," *Adhesives Age,* pp. 36 and 38–39 (Oct., 2000).

"PSTC–1, Peel Adhesion of Single Coated Pressure Sensitive Tapes 180° Angle," *Test Methods For Pressure Sensitive Adhesive Tapes, 12th Edition,* Pressure Sensitive Tape Council, Chicago, Ill., Title page, table of contents, and pp. 23–24 (1996).

Satas, D., ed., *Handbook of Pressure Sensitive Adhesive Technology,* 2nd Edition, Van Nostrand Reihold, New York, NY, Title page, publication page, and pp. 172–173 (1989).

*Test Methods For Pressure Sensitive Adhesive Tapes, 12th Edition,* Pressure Sensitive Tape Council, Chicago, Ill., Title page, table of contents, and pp. 2 and 6 (1996).

Wente, Van A., "Manufacture of Superfine Organic Fibers," *Report No. 4364 of the Naval Research Laboratories,* Title Page, publication page, and pp. 1–15 (May 25, 1954).

Wente, Van A., "Superfine Thermoplastic Fibers," *Industrial and Engineering Chemistry,* 48(8):1342–1346 (Aug., 1956).

Curad, Extreme Shapes, Bandages for fingertip, elbow/knee, or knuckle, Beiersdorf Inc., Wilton, CT 06897 (2000) (Photocopy of Packaging—2 pgs.).

Pressure Sensitive Tape Council Proceedings, 19th Annual Technical Seminar, Westin O–Hare, Rosemount, Illinois, 6 pp. (May 1–3, 1996).

\* cited by examiner

STRETCH REMOVABLE ADHESIVE ARTICLES AND METHODS

CROSS-REFERENCE TO RELATED APPLICATIONS

The present application is a Continuation-In-Part of U.S. application Ser. No. 09/764,540, filed on Jan. 17, 2001, now abandoned which is incorporated herein by reference in its entirety.

BACKGROUND OF THE INVENTION

The invention relates to pressure sensitive adhesive products, particularly stretch removable adhesive articles. Preferably, such articles are for use in adhering to skin or like delicate surfaces. Stretch removability occurs as a result of the selection of a stretch removable adhesive, i.e., one that has sufficient internal strength that it can be gripped and removed on its own even in the absence of a backing, or as a result of the selection of a stretch removable backing, i.e., a backing that allows a construction that includes a weaker adhesive to be removed by stretching.

Pressure sensitive adhesive tapes and the like are used in a wide variety of applications where there is a need to adhere to skin, for example, medical tapes, wound or surgical dressings, athletic tapes, surgical drapes, or tapes or tabs used in adhering medical devices such as sensors, electrodes, ostomy appliances, or the like. A concern with all these adhesive-coated products is the need to balance the objective of providing sufficiently high levels of adhesion to ensure that the pressure sensitive adhesive products do not fall off, while ensuring that the underlying skin or other delicate surface experiences a low amount of trauma, damage, or irritation during use and/or removal. These goals are generally conflicting. Many approaches have been suggested to balance these conflicting goals; however, there still remains a need for products that effectively do so.

For example, film-backed, normally tacky, pressure sensitive adhesive tapes that are highly stretchy and elastic are known that can be easily removed from a surface by stretching the tapes lengthwise in a direction substantially parallel to the plane of the surface. For such tapes the adhesion capability substantially disappears as the film is being stretched. If such tapes are too elastic, they may exhibit large recoil when the stretching force is removed, which can be undesirable. Additionally, highly elastic tapes tend to substantially recover their original shape when the stretching force is removed, and they are therefore not useful for indication of tampering or for guaranteeing single uses for hygienic purposes.

Such so-called "stretch release" or "stretch removable" adhesive constructions include backings having stretchabilities that typically match those of the adhesives. Other backings of differing stretchability can be used by using a pre-treated/damaged backing having a strength that is inconsequential in the stretch removal process and an adhesive that is substantial enough to alone support the stretch removal process, i.e., a stretch removable adhesive. Although many of such constructions are useful, there is still a need for stretch removable adhesive articles, particularly those that can be easily removed from a surface such as skin or other delicate surface without a significant amount of pain, trauma, damage, or irritation.

SUMMARY OF THE INVENTION

The present invention provides methods and stretch removable adhesive articles that include a backing and a pressure sensitive adhesive layer disposed thereon. Preferably, the adhesive itself is stretch removable. Preferably, the adhesive is one that is suitable for use on skin and the adhesive article is in the form of a medical article, such as medical tapes, wound or surgical dressings, athletic tapes, surgical drapes, tapes or tabs used in adhering medical devices such as sensors, electrodes, ostomy appliances, and the like.

In one general embodiment, the backing and adhesive are selected such that they delaminate upon removal from skin (or similar delicate surface). Typically and preferably, this involves selecting the backing and adhesive such that the stretchability of the adhesive layer is greater than that of the backing under the same tension. In another general embodiment, the backing includes a predefined tab (i.e., handle) located in a central portion of the backing, which can be used in a wide variety of adhesive articles, whether for medical or nonmedical uses.

More specifically with respect to one of the general embodiments, the present invention provides methods of removal, methods of making, and medical articles that delaminate upon removal from skin. One removal method involves: providing a medical article adhered to skin, wherein the medical article includes a backing and a stretch removable pressure sensitive adhesive layer disposed thereon; and stretching the medical article in an amount sufficient to delaminate the adhesive layer from the backing and remove the medical article from the skin. Preferably, stretching the medical article includes stretching it in a direction substantially parallel to the plane of the skin to which it is adhered. Preferably, the backing and adhesive are selected such that the stretchability at break of the adhesive layer is greater than that of the backing under the same tension, and more preferably, at least about 10% greater.

Another method of removing a medical article from skin that delaminates upon removal includes: providing a medical article adhered to skin, wherein the medical article includes a backing and a stretch removable pressure sensitive adhesive layer disposed thereon; and stretching the medical article in an amount sufficient to delaminate the adhesive layer from the backing and remove the medical article from the skin. In this embodiment: the backing and the adhesive layer are selected such that the stretchability of the adhesive layer is greater than that of the backing under the same tension; the stretch removable pressure sensitive adhesive layer includes a pressure sensitive adhesive matrix and a fibrous reinforcing material within the pressure sensitive adhesive matrix; and the adhesive layer has a yield strength and a tensile strength, and wherein the tensile strength is about 0.7 MPa or greater, and at least about 150% of the yield strength.

Yet another method of removing a medical article that delaminates involves: providing a medical article adhered to skin, wherein the medical article includes a backing and a stretch removable pressure sensitive adhesive layer disposed thereon; and stretching the medical article in a direction relative to the skin to which it is adhered sufficient to delaminate the adhesive layer from the backing and remove the article from the skin. In this embodiment: the backing and the adhesive layer are selected such that the stretchability of the adhesive layer is greater than that of the backing under the same tension; the stretch removable pressure sensitive adhesive layer includes a pressure sensitive adhesive matrix that includes a polymer derived from at least one alkyl ester monomer selected from isooctyl acrylate, 2-ethyl-hexyl acrylate, and n-butyl acrylate, and at least one co-monomer selected from acrylic acid and acrylamide; and a fibrous reinforcing material within the pressure sensitive adhesive matrix; and the adhesive layer has a yield strength and a tensile strength, and wherein the tensile strength is about 0.7 MPa or greater, and at least about 150% of the yield strength.

Preferably, a medical article that delaminates upon removal is provided and includes a backing and a stretch removable pressure sensitive adhesive layer disposed thereon. The backing and the adhesive layer are selected such that the stretchability of the adhesive layer is greater than that of the backing under the same tension and the adhesive layer and backing delaminate when removed from skin. Preferably, for enhanced delamination, the adhesive layer and backing form separate phases (i.e., are in separate layers).

For the articles that delaminate upon removal, the adhesive layer can include a wide variety of polymers, such as a poly(meth)acrylate (e.g., a polymer derived from at least one alkyl ester monomer selected from isooctyl acrylate, 2-ethyl-hexyl acrylate, and n-butyl acrylate, and at least one co-monomer selected from acrylic acid and acrylamide) or an A-B-A block copolymer. It can be reinforced as with a fibrous reinforcing material. Preferably, the adhesive layer includes: a pressure sensitive adhesive matrix; and a fibrous reinforcing material within the pressure sensitive adhesive matrix; wherein the adhesive layer has a yield strength and a tensile strength, and wherein the tensile strength is about 0.7 MPa or greater, and at least about 150% of the yield strength.

The present invention also provides a method of making a medical article that delaminates upon removal as described above. The method includes providing a backing; selecting a stretch removable pressure sensitive adhesive such that the stretchability of the adhesive layer disposed on the backing is greater than that of the backing under the same tension; and laminating the backing and the pressure sensitive adhesive layer together under conditions of temperature and pressure that allow the adhesive layer and backing to delaminate when removed from skin.

With respect to another general embodiment, the present invention also provides methods of removal, methods of making, and articles that include a predefined tab on the backing. Specifically, the present invention provides a stretch removable adhesive article that includes a backing with a predefined tab and a pressure sensitive adhesive layer disposed on a major surface of the backing opposite that of the tab, wherein the predefined tab is located in a central portion of the backing. Preferably, the pressure sensitive adhesive is a stretch removable pressure sensitive adhesive. More preferably, the backing and the adhesive layer are selected such that the stretchability of the adhesive layer is greater than that of the backing under the same tension, more preferably, at least about 10% greater.

For the articles that include a predefined tab, the adhesive layer can include a wide variety of polymers, such as a poly(meth)acrylate (e.g., a polymer derived from at least one alkyl ester monomer selected from isooctyl acrylate, 2-ethyl-hexyl acrylate, and n-butyl acrylate, and at least one co-monomer selected from acrylic acid and acrylamide) or an A-B-A block copolymer. It can be reinforced as with a fibrous reinforcing material. Preferably, the adhesive layer includes: a pressure sensitive adhesive matrix; and a fibrous reinforcing material within the pressure sensitive adhesive matrix; wherein the adhesive layer has a yield strength and a tensile strength, and wherein the tensile strength is about 0.7 MPa or greater, and at least about 150% of the yield strength.

The tab can be in a wide variety of shapes, sizes, and made of a wide variety of materials. In one preferred embodiment, the tab includes a portion of the backing and a portion of the adhesive layer. In another preferred embodiment, the backing includes two pieces (optionally overlapping pieces), preferably each with a nonadhesive end (i.e., an end free of exposed adhesive) that forms a tab.

In a preferred embodiment of the article with a predefined tab, the present invention provides a stretch removable adhesive article that includes a backing with a predefined tab and a stretch removable pressure sensitive adhesive layer disposed thereon, wherein the predefined tab is located in a central portion of the backing, and further wherein the backing and the adhesive layer are selected such that the stretchability of the adhesive layer is greater than that of the backing under the same tension. Preferably, the adhesive layer includes: a pressure sensitive adhesive matrix; and a fibrous reinforcing material within the pressure sensitive adhesive matrix; wherein the adhesive layer has a yield strength and a tensile strength, and wherein the tensile strength is about 0.7 MPa or greater, and at least about 150% of the yield strength.

The present invention also provides a method of removing an article having a predefined tab from a surface. The method involves: providing a stretch removable adhesive article adhered to a surface, wherein the article includes a backing with a predefined tab and a pressure sensitive adhesive layer disposed thereon, wherein the predefined tab is located in a central portion of the backing; and pulling on the tab to stretch the adhesive article in an amount sufficient to remove the article from the surface. Preferably, pulling on the tab is along a direction that is normal to the surface to stretch the adhesive article in an amount sufficient to remove the article from the surface. Preferably, the pressure sensitive adhesive is a stretch removable pressure sensitive adhesive. More preferably, the backing and adhesive are selected such that the stretchability of the adhesive layer is greater than that of the backing under the same tension.

In another method of removing an article from a surface, the method includes: providing a stretch removable adhesive article adhered to a surface, wherein the article comprises a backing and a pressure sensitive adhesive layer disposed thereon; and pulling on the article along a direction that is not normal to the surface to stretch the adhesive article in an amount sufficient to remove the article from the surface. Preferably, the direction forms an angle of about 20 degrees or more off of normal. Preferably, the article is rotated to a nearly perpendicular orientation from its starting position. Preferably, backing includes a predefined tab and pulling on the article includes pulling on the predefined tab, which is preferably located in a central portion of the backing.

There is also provided a method of making a medical article that involves: providing a backing with a predefined tab located in a central portion of the backing; and applying a stretch removable pressure sensitive adhesive to a major surface of the backing opposite that of the predefined tab. The step of applying can involve laminating, spray coating, etc.

In this application, the following terms are defined as follows, unless otherwise stated:

"Delamination" or "delaminate" means that, upon stretching an adhesive article, the adhesive separates (i.e., detaches) from at least a portion of the backing.

"Elastic" means how well a stretched material will recover. An elastic material is one that will recover by at least about 50% after being stretched in at least one direction, preferably by at least about 60%, more preferably by at least about 75%, and most preferably by at least about 100% after being stretched (i.e., it returns to its original size). An inelastic or nonelastic material is one that will recover by less than about 50% after being stretched.

"Stretchability" means how far a material can be elongated. A stretchable material is one that does not break upon elongating the material by at least about 20% in at least one direction. Unless otherwise stated, stretchability is assumed to be for elongation of a material in the lengthwise direction. A nonstretchable material is one that breaks upon stretching the material by less than about 20%. Percent stretchability (or elongation) at a given tension/force or at break can be measured by inspection of the plots generated via ASTM D3759 (1996) or D5459 (1995).

"Stretch removable" means that a pressure sensitive adhesive or article, when pulled and elongated (preferably from a substrate surface at a rate of 30 centimeters/minute and at an angle of no greater than 45°) detaches from a substrate surface without significant damage to the substrate surface (e.g., tearing), and without leaving a significant residue, preferably that which is visible to the unaided human eye on the substrate.

"Substantially continuous" means that for an at least 0.5 centimeter length sample of the adhesive composition taken in the machine direction, at least 50% of the fibers present in the sample are continuous (i.e., unbroken).

"Tensile strength" is the maximum tensile strength at break when tested according to ASTM D 882-97 at a crosshead speed of 12 inches/minute (30 centimeters/minute).

DETAILED DESCRIPTION OF PREFERRED EMBODIMENTS

Figure 1:
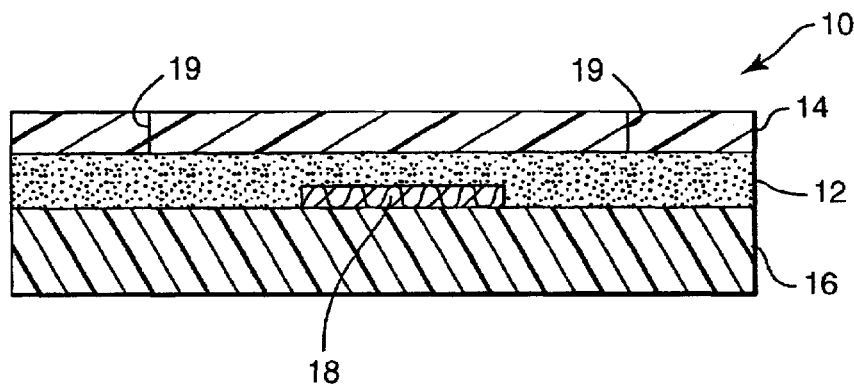
FIG. 1 is an enlarged side view in cross-section of an adhesive tape of the present invention that includes a backing, optionally perforated, in the unstretched position.

The present invention provides stretch removable adhesive articles, particularly adhesive articles that include a backing having a stretch removable pressure sensitive adhesive layer disposed on at least one major surface thereof. Preferably, the adhesive articles are designed for use on skin or other delicate surfaces with no significant damage to the skin or other delicate surface, and if the surface is skin, there is little or no pain upon removal of the adhesive article.

Preferably, such adhesive articles are tapes that include gauze pads, for example, and are used as first aid dressings (i.e., wound or surgical dressings). The adhesive articles can be in the form of a wide variety of other medical articles, such as medical tapes, athletic tapes, surgical drapes, or tapes or tabs used in adhering medical devices such as sensors, electrodes (as disclosed in U.S. Pat. No. 5,215,087 (Anderson et al.), and U.S. Pat. No. 6,171,985 (Joseph et al.), for example), ostomy appliances, or the like. Adhesive articles of the present invention can also be in the form of removable labels, coupons, masking tapes, tapes or tabs used in adhering diapers, packaging, food storage containers, etc. They can be used in tamper-indicating applications, particularly if upon stretching, the adhesive articles do not recover their original shape. Preferred embodiments, however, are medical articles.

Generally, adhesive articles (e.g., tapes) of the present invention are designed to be removed from a surface with concomitant delamination of the adhesive layer from the backing or by using a predefined tab located in a central portion of the backing (preferably, over a gauze pad). These designs provide significant advancements, particularly in the area of medical articles because of the ability to remove an adhesive article (e.g., bandage, tape) without significant pain, irritation, or injury to the underlying skin.

If delamination during removal is desired, the backing and adhesive are preferably selected such that the stretchability of the adhesive is greater than that of the backing. Preferably, the stretchability at break of the adhesive is at least about 10% greater than that of the backing. Generally, with conventional stretch removable adhesive articles the backing and the stretch removable adhesive are selected such that they stretch together for effective release; however, with adhesive articles of the present invention, delamination of the adhesive from the backing allows for a mismatch in stretch.

Selection of an adhesive and a backing for those embodiments in which delamination is desired involves evaluating each of their respective stretchabilities as well as their bonding capacity for each other and for the surface to which they are adhered. That is, the adhesive and backing are selected such that they have sufficient adhesion to each other and do not separate from each other prior to removal of the adhesive article from a surface to which it is adhered. Stretchability can be determined by measuring the elongation of a material or construction when pulled by a known force up to and including the point at break, such as by using an INSTRON machine according to ASTM D3759 (1996) or D5459 (1995). Preferably, the stretchability at break of the adhesive (layer) is at least about 100%, more preferably, at least about 300%, and most preferably, at least about 400%. Preferably, the stretchability at break of the adhesive is no greater than about 800%.

Preferred adhesive articles of the present invention have an initial adhesion to a surface, such as skin for medical articles, of at least about 20 grams per 2.5 centimeters (0.8 Newtons per decimeter), and more preferably, at least about 40 grams per 2.5 centimeters (1.6 N/dm). This can be evaluated, for example, using PSTC-1 Peel Adhesion Test, a testing protocol established by the Specifications and Technical Committee of the Pressure-sensitive Tape Council located at 5700 Old Orchard Road, Skokie, Ill.

Effective adhesion between the backing and adhesive can be determined by ASTM D1876 (1995). Preferred adhesives and backings of the present invention have an initial adhesion to each other of at least about 10 grams per 2.5 centimeters (0.4 Newtons per decimeter), and more preferably, at least about 20 grams per 2.5 centimeters (0.8 N/dm). This adhesion can be affected not only by the choice of materials but also by the lamination and/or coating process. For example, conditions of lamination and/or coating involve those wherein the adhesive layer and backing maintain separate layers (i.e., phases). That is, neither melting of the adhesive or backing occurs during the laminating process to form a separate continuous layer at the interface, nor does the adhesive deform and flow into the backing, as in a nonwoven web backing, for example.

Delamination means that, upon stretching an adhesive article, the adhesive separates (i.e., detaches) from at least a portion of the backing. Preferably, the adhesive separates from at least about 50% of the area of the backing, more preferably, the adhesive separates from at least about 60%, even more preferably, at least about 80%, and most preferably, at least about 95%, of the area of the backing, wherein the area of the backing is determined after the article is stretched and removed from a surface. Typically to accomplish delamination, the internal (i.e., structural) strength of the adhesive is greater than the adhesion of the adhesive to the backing. Delamination can be enhanced, for example, by laminating under low pressure and/or low temperature, eliminating pretreatment methods (e.g., corona treatment) typically used in preparing adhesive articles, by using a low adhesion backsize between the backing and the adhesive layer, by roughening the backing to lower the contact area between the backing and a stiff adhesive, etc.

Preferably, for effective delamination upon removal of an adhesive article from a surface, the lamination temperature during the manufacturing process of the adhesive article does not exceed the softening temperature of either the backing material or any reinforcing materials in the adhesive layer. Laminating above the softening temperature but below the melting temperature is typically not sufficient, since diffusion and adhesion can build up significantly above the softening temperature. For example, many ethylene vinyl acetate materials have melting temperatures about 60° C. to about 90° C. with softening temperatures about 40° C. to about 75° C.

Generally, delamination occurs upon stretching an adhesive article lengthwise in a direction substantially parallel to the plane of the surface to which it is adhered (prior to pulling), although this is not a necessary requirement to accomplish delamination (i.e., delamination can occur upon pulling and stretching the article in a direction from about 0° to about 90° from the surface to which it is attached). A simple test to determine if the backing and adhesive have sufficiently different stretchability to allow for delamination is to place a piece of the adhesive construction (1 centimeter by 4 centimeters) on a desired surface, for example, skin, a mirror-finished steel panel, or a polypropylene substrate, by rubbing down with light thumb pressure, optionally allowing for the adhesion to the substrate surface to build over a short period of time (e.g., about 10 minutes), and then pulling and stretching at a desired rate (for example, 30 or 152 centimeters per minute) at a desired angle (preferably at an angle no greater than about 45° from the plane of the adhesive bond, and more preferably lengthwise in a direction substantially parallel to the plane of the adhesive bond). The construction is then visually examined to determine if at least a portion of the area of the backing (after stretching) has been separated from the adhesive during removal. Because the backing can be stretched without recovery, the area of the backing used to make this evaluation is that after the stretch removal process.

In certain adhesive articles of the present invention, and independent of whether or not delamination occurs upon stretch removal, the backing includes a predefined tab located in a central portion of the backing (i.e., the about 80% of the mid portion of the backing along its length). Such adhesive articles having tabs can be used in a wide variety of applications, as discussed above. Typically, the adhesive article is removed by pulling the tab in a direction that is substantially normal to the plane of the surface to which the article is adhered (prior to pulling), although this is not a necessary requirement for effective functioning of the tab (i.e., removal can occur upon pulling the tab in a direction from about 0° to about 90° from the surface to which it is attached). With a tab (i.e., handle) in a central portion of a backing, the adhesive article typically does not get scraped over the wound as it is being removed as often can occur when it is pulled from an end across the wound. Preferably, by placing the tab in a central portion of the backing, the force of elongation can be distributed over two portions of the adhesive article (i.e., the two portions on either side of the tab).

Pressure Sensitive Adhesive

A wide variety of pressure sensitive adhesives can be used for this invention as long as they are stretch removable or are part of an adhesive article (i.e., adhesive construction) that is stretch removable. Preferably, the adhesive itself is stretch removable as defined above. Preferably, the stretch removable pressure sensitive adhesive is one that is suitable for use on skin, for example, acrylate polymers, natural and synthetic rubbers, silicone polymers, polyurethanes, polyolefins, and poly(vinyl ethers), as generally described in the article "Medical Adhesives: Adhesive Considerations for Developing Stick-to-Skin Products," *Adhesives Age*, October, 2000.

The pressure sensitive adhesive can be any material that has pressure sensitive adhesive properties. One well known means of identifying pressure sensitive adhesives is the Dahlquist criterion. This criterion defines a pressure sensitive adhesive as an adhesive having a 1 second creep compliance of greater than $1\times10^{-6}$ cm$^2$/dyne as described in *Handbook of Pressure Sensitive Adhesive Technology*, Donatas Satas (Ed.), $2^{nd}$ Edition, p. 172, Van Nostrand Reinhold, New York, N.Y., 1989. Alternatively, since modulus is, to a first approximation, the inverse of creep compliance, pressure sensitive adhesives may be defined as adhesives having a Young's modulus of less than $1\times10^6$ dynes/cm$^2$. Another well known means of identifying a pressure sensitive adhesive is that it is aggressively and permanently tacky at room temperature and firmly adheres to a variety of dissimilar surfaces upon mere contact without the need of more than finger or hand pressure, and which may be removed from smooth surfaces without leaving a residue as described in *Test Methods for Pressure Sensitive Adhesive Tapes*, Pressure Sensitive Tape Council, (1996). Another suitable definition of a suitable pressure sensitive adhesive is that it preferably has a room temperature storage modulus within the area defined by the following points as plotted on a graph of modulus versus frequency at 25° C.: a range of moduli from approximately $2\times10^5$ to $4\times10^5$ dynes/cm$^2$ at a frequency of approximately 0.1 radian/second (0.017 Hz), and a range of moduli from approximately $2\times10^6$ to $8\times10^6$ dynes/cm$^2$ at a frequency of approximately 100 radians/second (17 Hz) (for example see FIGS. 8–16 on p. 173 of *Handbook of Pressure Sensitive Adhesive Technology*, Donatas Satas (Ed.), $2^{nd}$ Edition, Van Nostrand Reinhold, New York, 1989). Any of these methods of identifying a pressure sensitive adhesive may be used to identify suitable pressure sensitive adhesives for use in the methods of the present invention.

Furthermore, the pressure sensitive adhesive layer of the adhesive articles of the present invention can be a single pressure sensitive adhesive or it can be a combination of two or more pressure sensitive adhesives. Suitable adhesives are inherently stretchy, as in styrene block copolymers, or they can be reinforced to increase cohesive strength and stretchability.

The adhesive articles of the present invention include a continuous layer or a discontinuous layer (e.g., porous layer) of a stretch removable pressure sensitive adhesive. This may result from solvent coating, screen printing, roller printing, melt spraying, stripe coating, or laminating processes, for example. Porosity can also occur by perforating a continuous adhesive layer. An adhesive layer can have a wide variety of thicknesses so long as it possesses pressure sensitive adhesive characteristics, and preferably, stretch removable pressure sensitive adhesive characteristics, with thicknesses preferably ranging from about 10 micrometers (i.e., microns) to about 1000 micrometers.

The pressure sensitive adhesive can be in the form of fibers intimately entangled each with the other in the form of a coherent breathable fibrous nonwoven adhesive web. Suitable nonwoven webs can be formed as melt blown microfiber webs using the apparatus discussed, for example, in Wente, Van A., "Superfine Thermoplastic Fibers," *Industrial Engineering Chemistry*, Vol. 48, pages 1342–1346, Wente, Van A. et al., "Manufacture of Superfine Organic Fibers," *Report No. 4364 of the Naval Research Laboratories*, published May 25, 1954, and in U.S. Pat. No. 3,849,241 (Butin et al.), U.S. Pat. No. 3,825,379 (Lohkamp et al.), and others. These microfine fibers are termed melt blown fibers or blown microfibers (BMF) and are generally substantially continuous and form into a coherent web between the exit die orifice and a collecting surface by entanglement of the microfibers due in part to the turbulent airstream in which the fibers are entrained. Other conventional melt spinning type processes, such as spunbond processes where the fibers are collected in a web form immediately upon fiber formation, can also be used to form the adhesive layer. Generally, the fibers are 100 microns or less in diameter when formed by melt spinning type processes, preferably 50 microns or less. The fibers, if formed by the melt blown process, can be produced as described in U.S. Pat. No. 5,176,952 (Joseph et al.); U.S. Pat. No. 5,232,770 (Joseph); U.S. Pat. No. 5,238,733 (Joseph et al.); U.S. Pat. No. 5,258,220 (Joseph); or U.S. Pat. No. 5,248,455 (Joseph et al.). The fibers can also be produced by a spunbond process as are disclosed in U.S. Pat. No. 5,695,868 (McCormach); U.S. Pat. No. 5,336,552 (Strack et al.); U.S. Pat. No. 5,545,464 (Stokes); U.S. Pat. Nos. 5,382,400; 5,512,358 (Shawyer et al.); or U.S. Pat. No. 5,498,463 (McDowall et al.).

Pressure sensitive adhesives useful in the present invention include, for example, those based on natural rubbers, synthetic rubbers, styrene block copolymers, polyvinyl ethers, poly(meth)acrylates (including both polyacrylates and polymethacrylates), polyolefins, and silicones. The pressure sensitive adhesive may be inherently tacky. If desired, tackifiers may be added to a base material to form the pressure sensitive adhesive. Useful tackifiers include, for example, rosin ester resins, aromatic hydrocarbon resins, aliphatic hydrocarbon resins, and terpene resins. Other materials can be added for special purposes, including, for example, oils, plasticizers, antioxidants, ultraviolet ("UV") stabilizers, hydrogenated butyl rubber, pigments, and curing agents.

Suitable stretchable block copolymers would include those formed using a tackified elastomer where a preferred elastomer is an A-B-A type block copolymer wherein the A blocks and B blocks are configured in linear, radial, or star configurations. The A block is formed of a monoalkenylarene (preferably polystyrene) block having a molecular weight of about 4000 to about 50,000. The A block content is preferably about 10 weight percent to about 50 weight percent. Other suitable A blocks may be formed from alpha-methylstyrene, t-butyl-styrene and other ring-alkylated styrenes, as well as mixtures thereof. The B block is formed of an elastomeric conjugated diene, generally polyisoprene, polybutadiene or copolymers thereof having an average molecular weight from about 5000 to about 500,000. The B block dienes can also be hydrogenated. The B block content is preferably about 90 percent to about 50 percent of the block copolymer. The tackifying components for the stretchable block copolymers generally are solid tackifying resins, liquid tackifiers, plasticizers, or mixtures thereof. Suitable liquid tackifiers or plasticizers for use in the adhesive polymer include napthenic oils, paraffin oils, aromatic oils, mineral oils or low molecular weight rosin esters, polyterpenes, and C-5 resins.

In a preferred embodiment, the pressure sensitive adhesive is based on poly(meth)acrylates (e.g., a polymethacrylic or polyacrylic pressure sensitive adhesive). Poly(meth) acrylic pressure sensitive adhesives are derived from, for example, at least one alkyl ester monomer such as, for example, isooctyl acrylate, isononyl acrylate, 2-methylbutyl acrylate, 2-ethyl-hexyl acrylate, and n-butyl acrylate; and an optional co-monomer component such as, for example, (meth)acrylic acid, vinyl acetate, N-vinyl pyrrolidone, (meth)acrylate, (meth)acrylamide, a vinyl ester, a fumarate, a styrene macromer, or combinations thereof. Preferably, the poly(meth)acrylic pressure sensitive adhesive is derived from about 0 to about 20 weight percent of acrylic acid and about 100 weight percent to about 80 weight percent of at least one of isooctyl acrylate, 2-ethyl-hexyl acrylate or n-butyl acrylate composition, preferably isooctyl acrylate. A particularly preferred embodiment for the present invention is derived from about 2 weight percent to about 10 weight percent acrylic acid, about 90 weight percent to about 98 weight percent of isooctyl acrylate, and about 2 weight percent to about 6 weight percent styrene macromer.

The poly(meth)acrylate pressure sensitive adhesives can be synthesized by a variety of free-radical polymerization processes, including solution, radiation, bulk, dispersion, emulsion, and suspension polymerization processes. Bulk polymerization methods, such as the continuous free radical polymerization method described in U.S. Pat. No. 4,619,979 (Kotnor et al.) or U.S. Pat. No. 4,843,134 (Kotnor et al.), the essentially adiabatic polymerization methods using a batch reactor described in U.S. Pat. No. 5,637,646 (Ellis), and the methods described for polymerizing packaged pre-adhesive compositions described in International Patent Application No. WO 96/07522 (Hamer et al.) may also be utilized.

The poly(meth)acrylate pressure sensitive adhesive of the present invention can include conventional additives such as tackifiers (wood rosin, polyesters, etc.), plasticizers, flow modifiers, neutralizing agents, stabilizers, antioxidants, fillers, colorants, and the like. Initiators that are not copolymerizable with the monomers used to prepare the (meth) acrylate copolymer can also be used to enhance the rate of polymerization and/or crosslinking. These additives are incorporated in amounts that do not materially adversely affect the desired properties of the pressure sensitive adhesives. Typically, they can be mixed into these systems in amounts of about 0.05 weight percent to about 25 weight percent, based on the total weight of the composition.

Pressure Sensitive Adhesive Reinforcing Material

In a preferred embodiment, the pressure sensitive adhesive is reinforced to increase the internal strength of the adhesive, and hence, its stretchability. This can be accomplished through the use of chemical or physical crosslinking, the addition of a second polymeric component having a higher glass transition temperature, or the addition of non-polymeric fillers (e.g., calcium carbonate, clay, zinc oxide) or the addition of fibers into the pressure sensitive adhesive. Suitable reinforced adhesives are disclosed in International Publication Nos. WO 97/23577 (Hyde et al.) and WO 96/25469 (Hyde et al.), U.S. Pat. No. 6,045,895 (Hyde et al.), and in Applicants' Assignee's copending U.S. patent application Ser. No. 09/764,478, entitled "Pressure Sensitive Adhesives and a Fibrous Reinforcing Material," filed on Jan. 17, 2001 as well as U.S. patent application Ser. No. 09/847,942, filed on May 2, 2001 and titled PRESSURE SENSITIVE ADHESIVES WITH A REINFORCING MATERIAL.

Preferably, the reinforced pressure sensitive adhesive has a yield strength of no less than about 0.1 MPa when measured according to ASTM D 882-97 at a crosshead speed of 12 inches/minute (30 centimeters/minute). In specific embodiments, the yield strength is no less than about 0.2 MPa when measured according to ASTM D 882-97 at a crosshead speed of 12 inches/minute (30 centimeters/minute). Additionally, the reinforced pressure sensitive adhesive (i.e., reinforced pressure sensitive adhesive composition) has a tensile strength of at least about 150% of the yield strength when measured according to ASTM D 882-97 at a crosshead speed of 12 inches/minute (30 centimeters/minute).

In certain embodiments of the preferred reinforced pressure sensitive adhesive, the tensile strength is about 0.7 MPa or greater when measured according to ASTM D 882-97 at a crosshead speed of 12 inches/minute (30 centimeters/minute). In specific embodiments of the preferred reinforced pressure sensitive adhesive, the tensile strength is about 0.8 MPa or greater when measured according to ASTM D 882-97 at a crosshead speed of 12 inches/minute (30 centimeters/minute). The adhesive composition may have a tensile strength of at least about two times greater than the tensile strength of the pressure sensitive adhesive alone when measured according to ASTM D 882-97 at a crosshead speed of 12 inches/minute (30 centimeters/minute).

For preferred embodiments, the elongation at break for the reinforced pressure sensitive adhesive composition is at least about 50% when measured according to ASTM D 882-97 at a crosshead speed of 12 inches/minute (30 centimeters/minute), preferably more than about 200%, and may be higher than about 300%. In some embodiments the elongation at break is in excess of about 800%.

Additionally, in preferred embodiments, the amount of force required to remove the adhesive composition from a polypropylene substrate at an angle of between 15° and 35°, is less than about 20 Newtons/decimeter. This low removal force permits facile removal of the adhesive composition from a substrate. In certain embodiments, the force necessary to remove the adhesive composition from a substrate at such an angle is as low as about 7 Newtons/decimeter.

Various reinforcing materials may be used in the pressure sensitive adhesive. In preferred embodiments, the reinforcing material is a polymer. In specific embodiments, the reinforcing material is elastomeric. Preferably, the reinforcing material is a semi-crystalline polymer. A semi-crystalline polymer is one having both amorphous and crystalline domains. Many specific embodiments incorporate semi-crystalline polymers, such as polycaprolactone (PCL), polybutene (PB), copolymers derived from ethylene and at least one other alpha-olefin monomer (e.g., poly(ethylene-co-1-alkene) and poly(ethylene-co-1-alkene-co-1-alkene)), ultra low density polyethylene (e.g., ATTANE 4202 commercially available from Dow Chemical Co.), linear low density polyethylene (e.g., LL-3003, ECD-125, 377D60, 369G09, 363C32, 361C33, 357C32, 350D65, 350D64, 350D60, LL-3013, and LL-3001 commercially available from Exxon Mobil Corp.) or combinations thereof.

Preferred reinforcing materials have a yield strength of less than about 20 MPa. The tensile strength of the reinforcing material with respect to its yield strength is preferably about 150% of the yield strength. These values are measured using ASTM D 882-97 at a crosshead speed of 12 inches/minute (30 centimeters/minute).

The reinforcing material preferably has a melting point above the use temperature of the adhesive composition. Similarly, the reinforcing material should have a melting point above the storage temperature of the adhesive composition or any article manufactured with the adhesive composition. Both the use temperature and the storage temperature should not exceed the decomposition temperature of the pressure sensitive adhesive. In certain embodiments, the reinforcing material has a melting point of at least 70° C. All temperatures are related as being measurable by differential scanning calorimetry ("DSC").

It is particularly desirable for the reinforcing material to have a melt viscosity similar to the melt viscosity of the pressure sensitive adhesive at the processing temperature of the method of this invention. In specific embodiments, the ratio of the reinforcing material melt viscosity to the pressure sensitive adhesive melt viscosity at the processing temperature is less than about 3, preferably less than about 1.5. In preferred embodiments, the ratio is between about 0.5 and about 1.2 depending on specific extrusion parameters (e.g. shear rate, screw speed, temperature). Melt viscosity is measurable as understood by one skilled in the art using a capillary viscometer.

The reinforcing material is preferably immiscible (i.e., remains in a separate phase) in the pressure sensitive adhesive during mixing so that the reinforcing material can be substantially uniformly dispersed (i.e., distributed) in the pressure sensitive adhesive. In specific embodiments, during mixing, the reinforcing material is in the form of substantially spherical particles having an average diameter less than about 20 micrometers, generally less than about 10 micrometers.

In preferred embodiments, the reinforcing material exists as substantially continuous fibers in the adhesive composition. Specifically, according to one aspect of the invention, the fibers are unbroken for at least about 0.5 centimeter in the machine direction of the pressure sensitive adhesive matrix, preferably about 2 to about 5 centimeters and more preferably about 8 centimeters. According to another aspect of the invention, the substantially continuous fibers generally have a maximum diameter of about 0.05 micrometer to about 5 micrometers, preferably from about 0.1 micrometer to about 1 micrometer. According to another aspect of the invention, the aspect ratio (i.e. the ratio of the length to the diameter) of the substantially continuous fibers is greater than about 1000.

Such preferred reinforced pressure sensitive adhesives are further described in Applicants' Assignee's copending U.S. patent application Ser. No. 09/764,478, entitled "Pressure Sensitive Adhesives and a Fibrous Reinforcing Material," filed on Jan. 17, 2001 as well as U.S. patent application Ser. No. 09/847,942, filed on May 2, 2001 and titled PRESSURE SENSITIVE ADHESIVES WITH A REINFORCING MATERIAL. A particularly preferred reinforced pressure sensitive adhesive is made according to Examples 1 and 2 of U.S. patent application Ser. No. 09/847,942, filed on May 2, 2001 and titled PRESSURE SENSITIVE ADHESIVES WITH A REINFORCING MATERIAL except with the use of 85% of the pressure sensitive adhesive and 15% EXACT 4023 (ethylene/butylene copolymer produced using a metallocene catalyst commercially available from Exxon Chemical Co., Houston, Tex.) and a basis weight of 50 grams per meter squared.

Backing

A wide variety of materials can be used to form the backing. The backing can be tearable or nontearable, elastic or inelastic, stretchable or nonstretchable, porous or nonporous. Backings can be in the form of single or multi-layer films, nonwoven films, porous films, foam-like films, and combinations of the foregoing. Backings can also be prepared from filled materials, such as, for example, filled films (e.g., calcium carbonate filled polyolefins).

Film backings can be made by any known method of film forming, such as, for example, extrusion, coextrusion, solvent casting, foaming, nonwoven technology, and the like. A backing can have a wide variety of thicknesses so long as it possesses sufficient integrity to be processable and, preferably, capable of forming tabs or having tabs attached thereto, with thicknesses preferably ranging from about 10 micrometers (i.e., microns) to about 250 micrometers.

Webs made from natural or synthetic fibers or mixtures thereof can be used. Woven or nonwoven materials can be employed, with nonwoven materials being preferred for most applications. Melt-blown or spunbond techniques can be employed to make such nonwoven webs. Nonwoven webs can also be prepared on a Rando Webber (Rando Corporation, Macedon, N.Y.) air-laying machine or on a carding machine.

If the backing substrate is in the form of a laminate, additional components could be used, such as absorbent layers (e.g., gauze pads) for adhesive bandage products, or the like. If absorbent layers are used, they are typically thin, coherent, conformable, and able to flex and not interfere with the stretch removable characteristics of the articles, although they can be stretchable or not.

If a laminate, there may be one or more additional layers, which can be a breathable, liquid impervious film. Typically this film is the outermost (i.e., top) layer. Examples of film materials include polyurethanes, polyolefins, metallocene polyolefins, polyesters, polyamides, polyetheresters, and A-B-A block copolymers, such as KRATON copolymers available from Shell Chemical Co. Preferably, the outermost layer is a film that is substantially impervious to fluids, such as could arise from the external environment, yet permit passage of moisture vapor, such that the adhesive article is breathable (typically, having a moisture vapor transmission rate (MVTR) of at least about 500 g/m$^2$/day).

A preferred film backing is a 3.5-mil (89-micron) fluted elastic available from Minnesota Mining and Manufacturing Company, Personal Care and Related Products Division, St. Paul, Minn. (Product No. XME 01-038 High Stretch Fluted Stretch Activated Elastic). Such a material can be made according to Example 7 of U.S. Pat. No. 5,462,708 (Swenson et al.) with the following exceptions: the core composition includes a block copolymer commercially available under the trade designation KRATON 1114 from Shell Oil Co. instead of KRATON 1657 and 30% styrene commercially available under the trade designation PS-678C from Dow Chemical Co. instead of 10% PS-615; the skin composition includes polypropylene commercially available under the trade designation ERD 1057 from Dow Chemical Co. instead of PP 1024; a C/S ratio of 6 instead of 5; and no delamination process as described in U.S. Pat. No. 5,462,708 at column 10, lines 21–38.

The backing can optionally include fibers, which may be absorbent or nonabsorbent, and typically they are non-water absorptive. The fiber structures useful in the backing substrate of the present invention can include a multilayer configuration, a coated configuration, and a solid homogeneous configuration. Suitable multilayer fibers preferably have cores and outer layers composed of one or more polymers selected from polyolefins, polyesters, polyamides, and polyurethanes. Suitable coated fibers preferably have cores made of these polymers with coatings covalently bonded, embedded, or adhered thereto. The homogeneous fibers preferably are made of any of the polymers listed above. Such fibers can be formed into backings using known weaving, knitting, or nonwoven techniques. Suitable such backings are disclosed, for example, in U.S. Pat. No. 5,613,942 (Lucast et al.).

In a preferred embodiment, the backing is formed from coherent multicomponent fibers having at least one pressure sensitive adhesive region or layer and at least one non-pressure sensitive adhesive region or layer as described in U.S. Pat. No. 6,107,219 (Joseph et al.). In another preferred embodiment, the backing is a melt blown polyprolyene web available from Kimberly Clark, Irving, Tex.

Typically, fibers forming a nonwoven tape backing are intimately entangled each with the other in the form of a coherent breathable fibrous nonwoven tape backing. Suitable nonwoven tape backings can be formed as melt blown microfiber webs using the apparatus discussed, for example, in Wente, Van A., "Superfine Thermoplastic Fibers," Industrial Engineering Chemistry, Vol. 48, pages 1342–1346, Wente, Van A. et al., "Manufacture of Superfine Organic Fibers," Report No. 4364 of the Naval Research Laboratories, published May 25, 1954, and in U.S. Pat. No. 3,849,241 (Butin et al.), U.S. Pat. No. 3,825,379 (Lohkamp), and others. These microfine fibers are termed melt blown fibers or blown microfibers (BMF) and are generally substantially continuous and form into a coherent web between the exit die orifice and a collecting surface by entanglement of the microfibers due in part to the turbulent airstream in which the fibers are entrained. Other conventional melt spinning type processes, such as spunbond processes where the fibers are collected in a web form immediately upon fiber formation, can also be used to form the invention nonwoven tape backing. Generally, the fibers are 100 microns or less in diameter when formed by melt spinning type processes, preferably 50 microns or less. The multicomponent fibers, if formed by the melt blown process, can be produced as described in U.S. Pat. No. 5,176,952 (Joseph et al.); U.S. Pat. No. 5,232,770 (Joseph); U.S. Pat. No. 5,238,733 (Joseph et al.); U.S. Pat. No. 5,258,220 (Joseph); or U.S. Pat. No. 5,248,455 (Joseph et al.). The multicomponent fiber can also be produced by a spunbond process as are disclosed in U.S. Pat. No. 5,695,868 (McCormach); U.S. Pat. No. 5,336,552 (Strack et al.); U.S. Pat. No. 5,545,464 (Stokes); U.S. Pat. Nos. 5,382,400; 5,512,358 (Shawyer et al.); or U.S. Pat. No. 5,498,463 (McDowall et al.).

In preferred embodiments of the present invention in which a stretch removable article can be prepared without a stretch removable adhesive, the backing is an elastic nonwoven web, as disclosed in U.S. Pat. No. 5,629,079 (Battles et al.). These elastic nonwoven webs include blown microfibers formed by extrusion of thermoplastic elastomers through a die, which produces fine, randomly oriented fibers. Several different constructions of webs are suitable for use in this embodiment of the invention. In multilayered blown microfibers, the elastic nonwoven web includes longitudinally layered melt-blown microfibers with layers of a low modulus or elastomeric materials and adjacent layers of heat bondable materials. In commingled blown microfibers, the elastic nonwoven web includes at least two different types of melt-blown microfibers. A first microfiber includes a low modulus or elastomeric material; a second microfiber includes a heat bondable material. In blown microfiber web having intertangled staple fiber, an elastomeric nonwoven web is produced using an elastomeric blown microfiber and a larger-diameter staple fibers. The elastomeric microfibers and staple fibers of the resulting web are generally randomly intermixed and intertangled. All three embodiments can be used in stretch removable articles of the present invention, particularly in embodiments in which the adhesive is not necessarily stretch removable.

Representative examples of materials suitable for the backing of the adhesive article of this invention include polyolefins, such as polyethylene, including high density polyethylene, low density polyethylene, linear low density polyethylene, and linear ultra low density polyethylene, polypropylene, and polybutylenes; vinyl copolymers, such as polyvinyl chlorides, both plasticized and unplasticized, and polyvinyl acetates; olefinic copolymers, such as ethylene/methacrylate copolymers, ethylene/vinyl acetate copolymers, acrylonitrile-butadiene-styrene copolymers, and ethylene/propylene copolymers; acrylic polymers and copolymers; polycaprolactones; and combinations of the foregoing. Mixtures or blends of any plastic or plastic and elastomeric materials such as polypropylene/polyethylene, polyurethane/polyolefin, polyurethane/polycarbonate, polyurethane/polyester, can also be used. Additionally, any nonstretchable material can be used for the tearable backings or for those with perforations, including paper and even metal. Preferred materials for the backing include polyurethane, polypropylene, ethylene vinyl acetate, or combinations thereof (e.g., blends, mixtures, etc.) in the form of melt blown fibers. Preferred materials for film backings include polycaprolactones and copolymers of ethylene/vinyl acetate and linear low density polyethylene.

The backing can have perforations or holes to provide porosity or for assisting in removing the adhesive articles or in delamination. These perforations may be in a variety of shapes (e.g., circular, rectangular, oval) and sizes and positioned in various predetermined locations depending on the desired break points upon removal of the adhesive article. For example, perforations can be located in the backing near a centrally located gauze pad so that pulling on the gauze pad causes the backing to break, and the pad/backing/adhesive act as a tab to remove the remainder of the article by stretching. Such perforations can be made using well known techniques. They can be partially or completely occluded, closed, or masked until stretching of the article. The perforations are typically of a size that does not allow the adhesive to extend through and impart tackiness to the opposite surface on which the adhesive is disposed. Preferably, the perforations are at least about 0.0025 centimeter (cm) in diameter, more preferably, at least about 0.01 cm, and most preferably, at least about 0.02 cm in diameter. Preferably, the perforations are not greater than about 0.04 cm in diameter.

Figure 2:
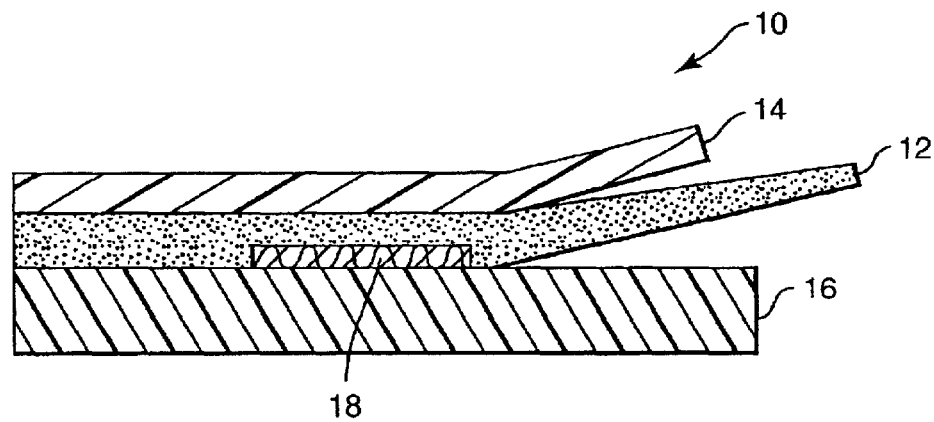
FIG. 2 is an enlarged side view in cross-section of an adhesive tape with the adhesive having been stretched and beginning to be removed from the substrate and delaminate from the backing.
Figure 3:
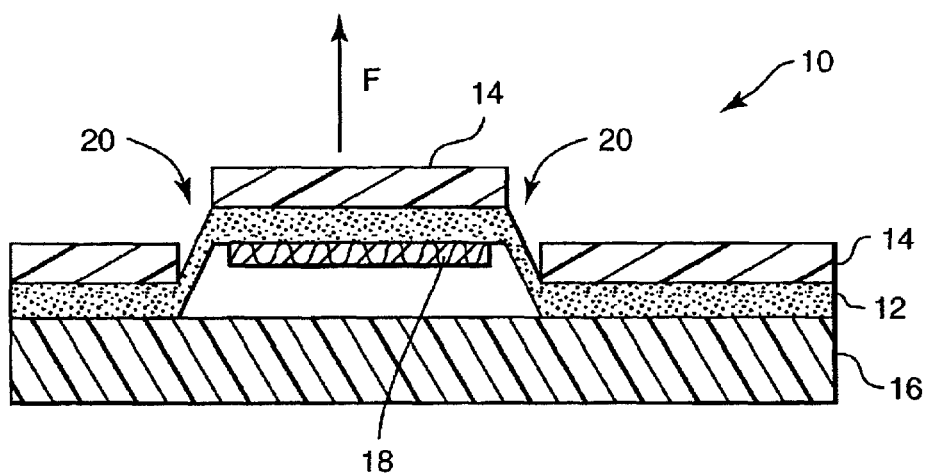
FIG. 3 is an enlarged side view in cross-section of a first aid dressing of the present invention that includes a perforated backing with perforations near the gauze pad with the backing having been broken and the adhesive having been stretched and beginning to cease holding to both the substrate and the backing.

Referring to FIGS. 1–3, an adhesive construction (e.g., tape) 10 of this invention includes a backing 14 bearing on at least one major surface thereof a pressure sensitive adhesive layer 12, which is preferably stretch removable. As shown in FIG. 1, tape 10 is adhered to substrate 16 and includes an optional gauze pad 18, for example, in the form of a wound dressing. As shown in FIG. 1, the backing is optionally perforated along lines 19. If desired, in this and other embodiments described herein the adhesive and/or backing over the pad 18 need not necessarily be stretchy. Also, the gauze pad may or may not be stretchy.

As shown in FIG. 2, during removal, the tape 10 is stretched substantially parallel to the substrate 16 surface and the adhesive layer 12 elongates and stretch releases from the substrate 16 and delaminates from at least part of the backing 14. If the adhesive construction includes perforations 19 in the backing 14, the perforated backing can tear (i.e., break) (not shown in FIG. 2).

As shown in FIG. 3, if the backing 14 possesses perforations (previously located at the points of break 20 in the backing 14) near the pad 18, the backing 14 can break at both sides of the pad 18 on stretching the construction (for simplicity, delamination of the adhesive 12 from the backing 14 is not shown except at the break points 20) by applying a pulling force along the direction of line F on the region of the tape 10 that encompasses the pad 18, which could also include a tab as discussed in greater detail below. An alternative embodiment of such a construction would not necessarily have perforations but could be removed in a similar fashion.

An image, if desired, can be placed on the adhesive portion of the construction and will be made visible on breaking the backing and stretching (not shown).

Tabs

The backings of the present invention may be equipped with tabs or handles in the form of grip ledges, folds, loops, and other devices to facilitate removal of the adhesive article (e.g., tape or wound dressing). The use of such tabs may be advantageous in obviating the need for prying (using a finger nail, for example) the end or center of an adhesive article from a surface prior to removal. Preferably, such tabs are located in a central portion of the backing (i.e., the center 80% of the length of a backing), and more preferably over the pad area if it is present.

The tabs can be in a variety of shapes and sizes. They can be made of a thin, highly flexible film that does not snag on environmental objects. The tabs may also be made by securing a ribbon of thin film or a thread under a bar of adhesive applied across the width of the backing. The tabs may also be formed from other parts of the backing, such as simply by making a fold in the backing during manufacture, which can be done before or after application of the adhesive. If the tab is formed after the adhesive is applied to the backing, the tab can include a portion of the adhesive. Alternatively, the backing can be in the form of two pieces, optionally with overlapping ends, each of which have a nonadhesive portion, i.e., a portion free of exposed adhesive. These ends can be free of adhesive or have a piece of liner covering the adhesive at the ends.

The preferred centrally located tabs are particularly advantageous for the removal of a wound dressing as they can reduce the pain of removal and allow careful avoidance of damage to the wounded area during removal. Such tabs are preferably pulled at about 45° up to right angles (i.e., normal) to the substrate and surface to which the adhesive article is attached, although this angle may be reduced to near zero (i.e., substantially in the plane of the adhesive bond) if the surface is not rigid (e.g., skin). Accordingly, a gauze pad of a wound dressing, for example, can clear the delicate central area of the wound first and typically can be prevented from scraping over the wound. Furthermore, the gentle pressures that result from releasing the dressing act to hold the wound shut. Advantageously, the tearing effect on the wound of customary dressing removal is typically avoided. The articles and methods of removal that utilize tabs are advantageous in that they prevent digging under one end of the adhesive tape "wings" of a wound dressing and peeling from one end to the other. Pain typically results from digging out hair or skin with the fingernails, from tearing out hair stuck to the dressing adhesive during the peeling operation, and from tearing at the edges of the wound.

Desirably, unpleasant and possibly septic or virus-containing wound exudate can be contained and concealed from view by the pinching action of removal that results in the dressing ending up folded in half widthwise and adhered together with the exudate inside. This removal action can be done with one hand. The method is quick, clean, gentle, and generally painless, and thus especially suited for children and the elderly.

The tab (i.e., handle) is preferably designed such that snagging or picking does not remove the adhesive article prematurely, for example, and that it indicates which direction to pull to get the benefit of the invention. Preferably, the tab is secured permanently in one area and temporarily in one or more other areas or is made in situ from other parts of the dressing during manufacture. The temporary securement of part of the tab is to prevent snagging and hooking. The tab may be colored to show where it is, and it may be printed with an arrow showing which way to pull it to get the painless removal benefit. Further directions could be on the wrapper or the box containing the medical articles.

Depending on the application, the tabs of the adhesive articles can be placed at different locations for advantageous removal. For example, in one preferred embodiment, a medical article is designed for adhesion to relatively loose skin, such as on the top of the forearm. In this embodiment, the point of attachment of the tab is generally symmetrically straddling the center gauze pad and centered in the long dimension of the dressing. In another preferred embodiment a medical article is designed for adhesion to skin that is relatively taut, as on the palm of the hand. In this embodiment, the point of attachment of the tab is preferably centered across the width of the pad, but located off center relative to the length of the article (although still within the central portion of the adhesive article).

Referring to FIGS. 4–9, various preferred embodiments of a wound dressing (e.g., approximately 1.9 cm by 7.6 cm) are shown that include a backing (e.g., PGI 6012 Comfort Silk Film from Polymer Group, Inc., Gainesville, Ga.), an adhesive layer (e.g., Adhesive A described in the Examples Section), and central gauze pad material (e.g., approximately 1.3 cm by 2.5 cm of a pad of an 108 gram/square meter absorbent rayon nonwoven laminated on both sides with P530S DELNET commercially available from Applied Extrusion Technologies, Middletown, Del.). Each embodiment demonstrates a different tab construction.

Figure 4:
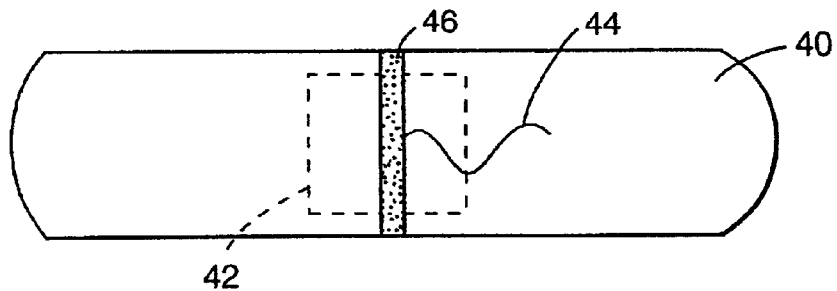
FIGS. 4–11 are representations of embodiments of the adhesive articles of the present invention having various types of tabs.

Referring to FIG. 4, the backing 40 of a preferred wound dressing is shown with a gauze pad 42 positioned on the opposite side of the backing 40 (shown by the hatched lines) and a tab 44. The tab 44 could be a string, thread, or polymer ribbon film (e.g., mercerized sewing thread) fixed to the backing 40 on the surface opposite the pad 42 with a bead of adhesive 46 (e.g., epoxy), preferably reaching from one side of the backing to the other across the narrow dimension (i.e., the width). The thread-shaped tab 44 is shown attached at the center along the length of the backing 40. Alternatively, it can be attached off center along the length of the backing 40, if desired.

Figure 5:
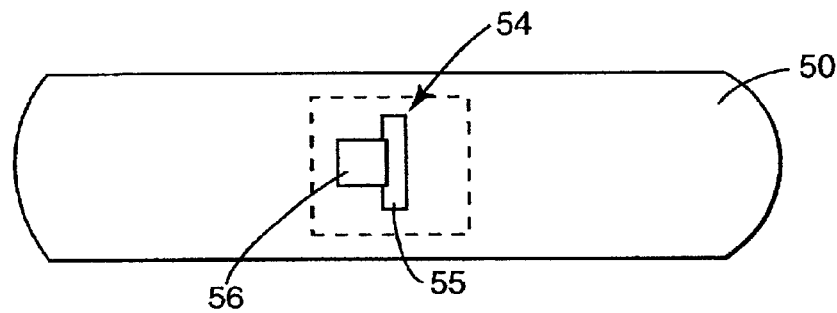

Referring to FIG. 5, the tab 54 could be made of thin polyester or other film shaped like a "T" and fixed across the width of the backing 50 with adhesive under or incorporating the top of the "T." The T shown in FIG. 5 is made of 0.5-mil (12.5-micron) polyester film and has a distance across portion 55 (or crossbar) of the T of 13 mm and the widths of the arms are 2 mm each. The portion 55 of the T is approximately centered on the long dimension of the pad and is adhered to the backing 50 with an adhesive (e.g., an adhesive commercially available from 3M Company, St. Paul, Minn., under the trade designation SUPER STRENGTH ADHESIVE) to form a permanent bond. Alternatively, the portion 55 of the T could be attached off center along the length of the backing 50, if desired. The portion 56 of the T is variable in length, but is preferably at least about 7 mm for ease of grasping, and is temporarily anchored to the backing 50 with an adhesive (e.g., an adhesive commercially available from 3M Company under the trade designation SCOTCH RESTICKABLE ADHESIVE glue stick) to form a nonpermanent bond.

Figure 6:
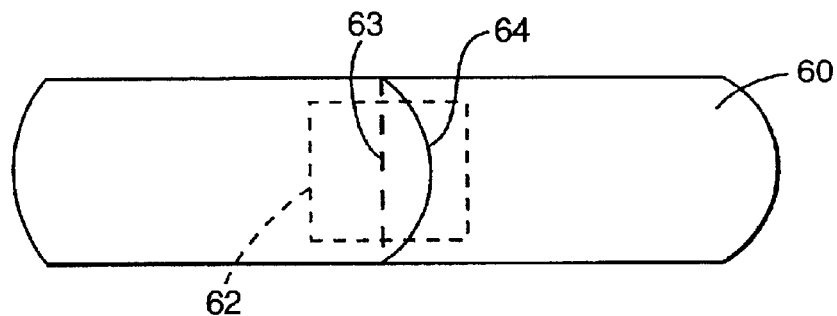

Referring to FIG. 6, the tab 64 is a half loop (rectangular or rounded) of material (e.g., thread) the open ends of which are fixed to the backing 60 midway along its length such that the resulting loop straddles an underlying gauze pad 62 symmetrically. Alternatively, the half loop-shaped tab 64 can be attached off center along the length of the backing 60, if desired. In this embodiment, the material of the tab 64 is thread and can be permanently adhered to the backing between the gauze pad 62 and the backing 60 (e.g., using 3M SUPER STRENGTH ADHESIVE) in a manner such that the thread would not touch the wound (as shown by hatched line 63). The half loop-shaped tab 64 can be temporarily adhered to the backing 60 (e.g., using SCOTCH RESTICKABLE ADHESIVE glue stick) until the adhesive article is to be removed. Passing these loop-shaped tabs between the pad and the backing could help distribute the load when fragile backings and adhesives are used. They could be completely impregnated with adhesive when used in this way to avoid wicking wound exudate out from under the dressing.

Figure 7:
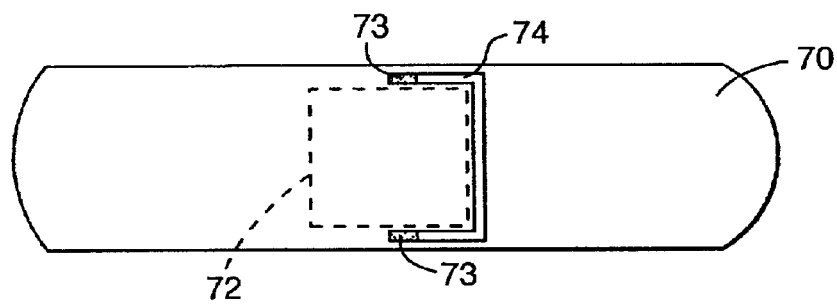

Referring to FIG. 7, the tab 74 is a rectangular or rounded half loop of material (e.g., 0.5-mil (12.5-micron) polyester film) the open ends of which are fixed to the backing 70 across its width so that the resulting loop straddles the underlying gauze pad 72, but is located at one end of the pad 72. The ends 73 (shaded) of the tab 74 are permanently adhered to the backing 70 (e.g., using 3M SUPER STRENGTH ADHESIVE) and the remainder can be temporarily adhered to the backing 70 (e.g., using SCOTCH RESTICKABLE ADHESIVE glue stick) until the adhesive article is to be removed.

Figure 8:
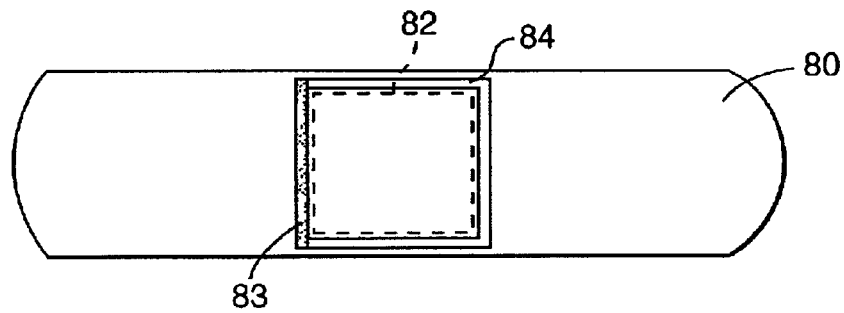

Referring to FIG. 8, the tab 84 is a rectangular shaped film (e.g., 0.5-mil (12.5-micron) polyester film) surrounding the underlying gauze pad 82. The tab 84 is permanently adhered along one edge 83 (shaded edge) (e.g., using 3M SUPER STRENGTH ADHESIVE) so one part of the rectangular-shaped tab 84 sticks to the backing while the other part lifts up. The tab could be a part of the backing cut to form a half moon shaped tab, for example, and easily picked up with a fingernail.

Figure 9:
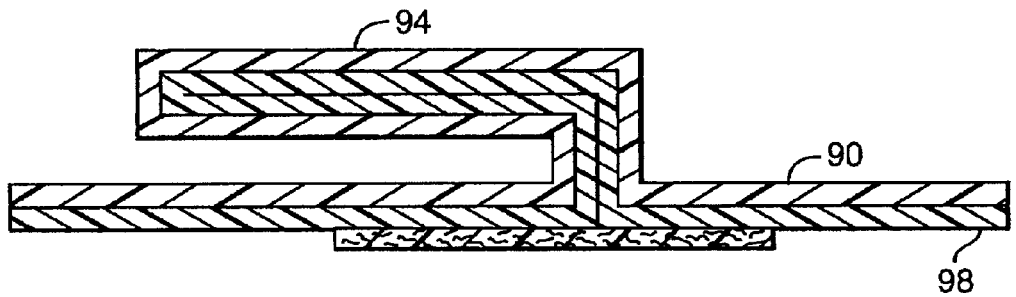

Referring to FIG. 9, a tab 94 is shown in cross-section that is formed from the backing 90, as can be done by making a fold in the backing during manufacture, either before or after application of the adhesive. In this embodiment the fold was made after the adhesive 98 was applied, thereby resulting in adhesive within the tab 94.

Figure 10:
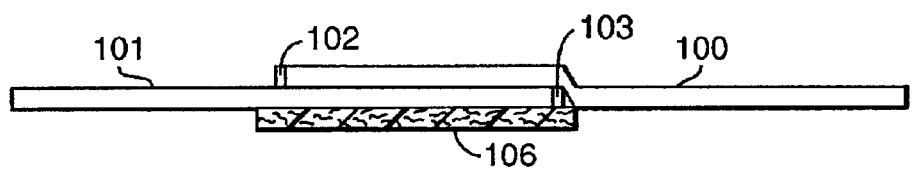
Figure 11:
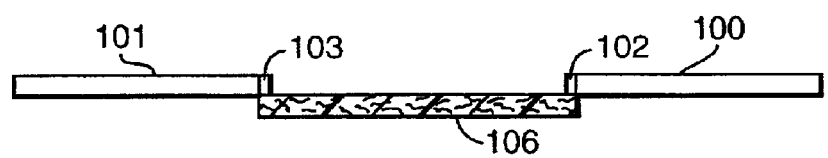

FIGS. 10 and 11 show two wound dressing constructions made from a tape construction as described in Example 1C in the Examples Section, the central pad 106 material being an 108 gram/square meter absorbent rayon nonwoven laminated on both sides with P530S DELNET commercially available from Applied Extrusion Technologies, Middletown, Del. Tabs 102 and 103 are 3 mm wide oriented polypropylene film commercially available as PROPORE KN9400 film from 3M Company, St. Paul, Minn.

In FIGS. 10 and 11 the backing can be in the form of two adhesive-coated pieces 100 and 101 with ends that have a nonadhesive portion in the form of tabs 102 and 103 that can overlap each other over the gauze pad 106 (as shown in FIG. 10) or not (as shown in FIG. 11). Each end forms a tab 102 and 103 for the respective backing piece 100 and 101. Referring to the embodiment shown in FIG. 10, for example, to remove the article, tab 102 is first pulled outward (i.e., away from tab 103) at an angle of about 10° allowing the adhesive to release from backing piece 101 over the pad 106, while backing piece 100 is removed from the skin. After removal of backing piece 100, the pad 106 can be folded under to form a handle for removal of backing piece 101 by stretching in a direction toward the area of removed backing piece 100. Alternatively, tab 103 can be grasped instead of folding the pad 106.

These descriptions of tab forms are not intended to be complete as other tab constructions could be used to pull up in the central position of the adhesive article.

For certain of the preferred wound dressings described above, it is useful to use a stretchable gauze pad. A stretchable gauze pad stays adhered to the deformable tape construction better than a non-stretchy pad, and the stretch removal behavior is communicated from one adhesive wing of the dressing to the other when a stretchy pad is used. This is especially true when an island pad occupying a large fraction of the width of the dressing is used.

Alternative Removal Methods

Adhesive articles of the present invention can be removed from a surface using a variety of techniques. For example, the article can be pulled along a direction that is normal to the surface to which it is adhered to stretch the adhesive article in an amount sufficient to remove the article from the surface. Alternatively, the article can be pulled along a direction that is not normal (and preferably, 20 degrees or more off normal) to the surface to which it is adhered. Generally, normal to the surface refers to an axis that is perpendicular to the surface, if the surface is generally planar, or an axis that is normal to a plane that is generally tangent to the surface, if the surface is generally curved. For embodiments in which the adhesive article is a wound dressing and the surface is skin, normal to the surface refers to the plane of the skin prior to pulling on the adhesive article (i.e., the "starting position" of the article).

Figure 12:
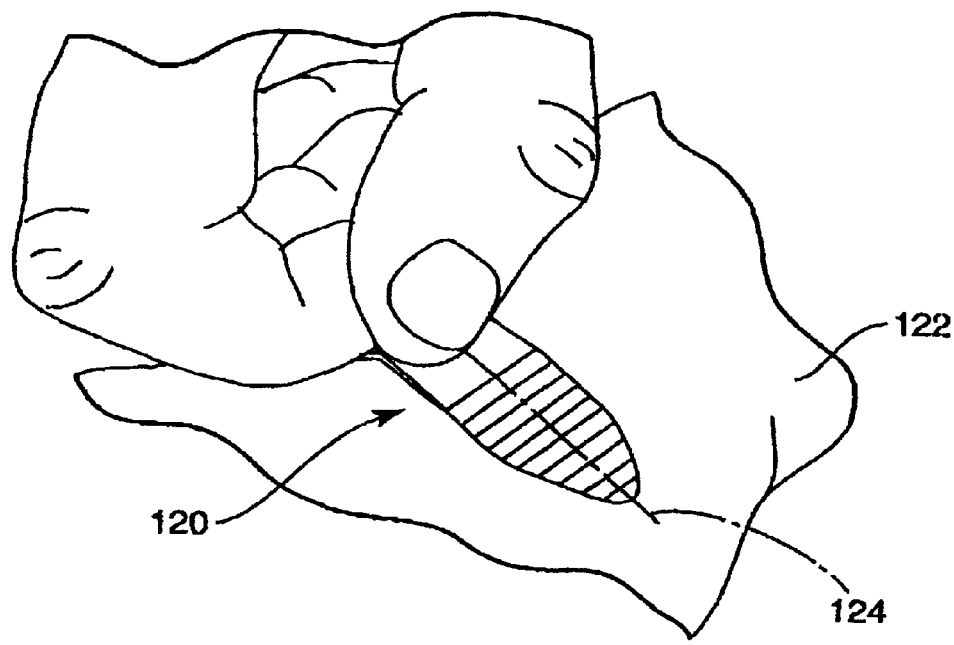
FIGS. 12–14 are representations of alternative removal methods of adhesive articles of the present invention.

FIG. 12 shows a wound dressing 120, such as that shown in FIG. 9, with a center tab (94 in FIG. 9, not shown in FIG. 12) being grasped by the thumb and index finger of an individual removing the dressing from a subject. The wound dressing 120 is then typically removed from the skin 122 of the subject by pulling, generally in a direction that is normal to the plane of the skin of the subject, and stretching the dressing so the adhesive releases from the skin. This pull and stretch is generally along the longitudinal center-line axis 124 of the wound dressing 120.

Figure 13A:
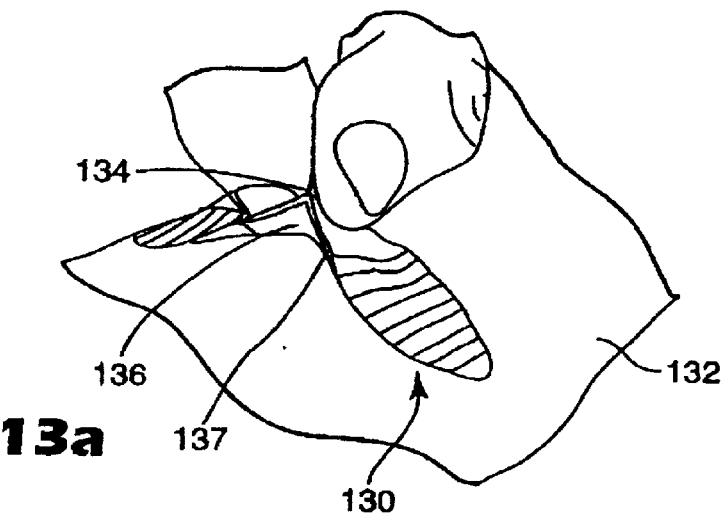
Figure 13B:
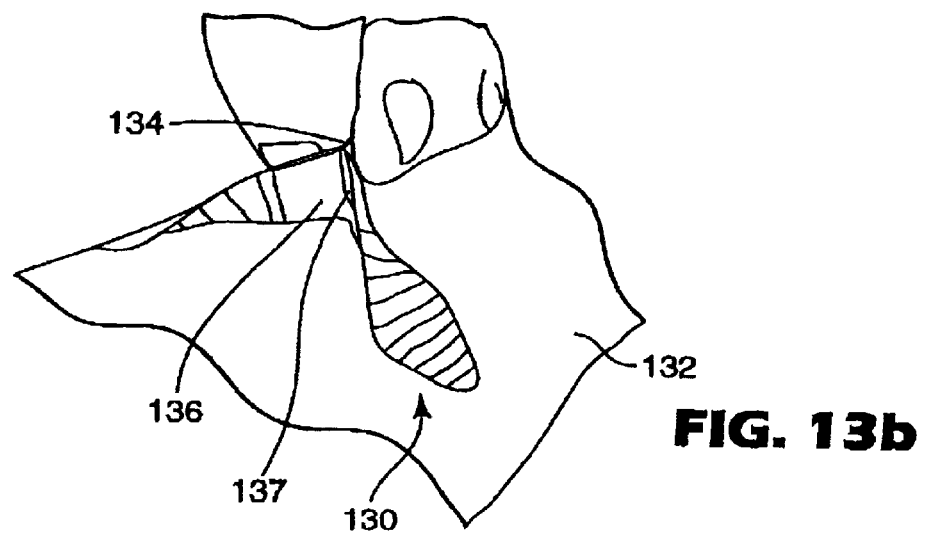
Figure 13C:
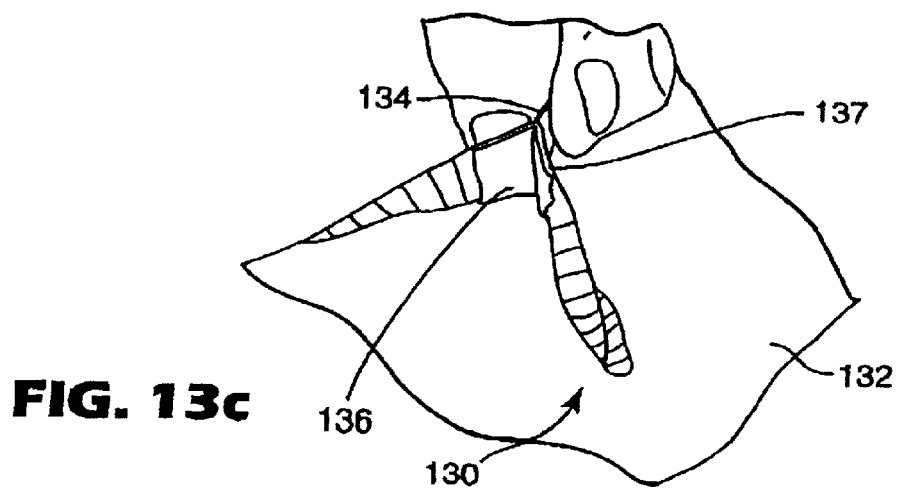

FIGS. 13a, 13b, and 13c show three progressive stages of an alternative method for the removal of a wound dressing 130 from the skin 132 of a subject. After grasping the center tab 134 of the wound dressing 130, the plane of the center pad 136 is rotated to a nearly perpendicular orientation from its starting position such that one edge 137 of the pad 136 is lifted away from the skin 132 of the subject. The opposing edge of the pad 136 typically remains proximate the skin 132. The center tab 134 is pulled in a direction that is not perpendicular (i.e., not normal) to the plane of the skin of the subject, causing the bandage to peel and stretch release from the skin. Although this method shows the center pad and center tab being rotated, this rotation is not a necessary requirement, as shown in the following figure.

Figure 14:
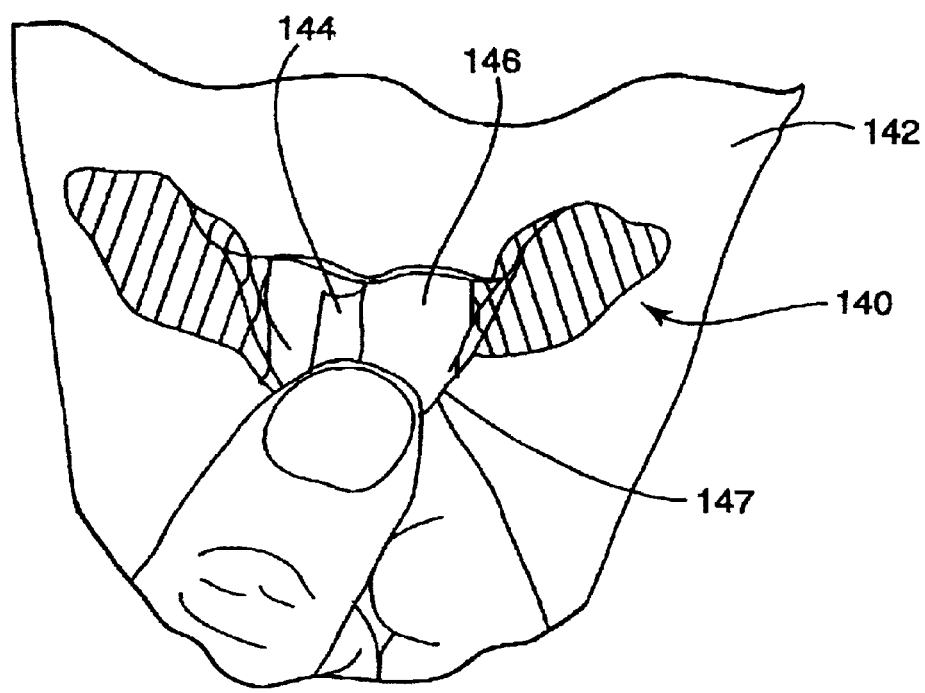

FIG. 14 shows another alternative method of the removal of a wound dressing 140 from the skin 142 of a subject. The center tab 144 and center pad 146 are grasped along the edge 147 of the pad 146 and the plane of the center pad 146 stays substantially parallel to the plane of the skin. The wound dressing is pulled in a direction substantially perpendicular to the center axis of the wound dressing and along the plane of the skin causing the bandage to peel and stretch release along the plane of the skin. That is, the wound dressing is pulled along a direction that is not normal to the skin.

Absorbent Particles and Other Additives

Wet skin adhesion characteristics of the adhesive articles of the present invention can be provided by an absorbent particulate material, typically in the form of a powder or larger particles, including fibers, herein referred to generally as particulate material or particles. The particles can be of any desired shape, such as round, flake-like, elongated, or irregular, for example. The particulate matter can be distributed uniformly throughout the backing substrate or can be coated onto either major surface of the backing. A sufficient amount of absorbent particulate material is present in or on the backing substrate to provide the desired levels of wet skin adhesion.

The particulate material is sufficiently water absorptive to provide articles having sufficient wet skin adhesion, preferably, at least about 20 g/2.5 cm (0.08 N/cm). Preferably, the particulate material is superabsorbent. Suitable superabsorbent particles are made from polymers that are capable of absorbing at least about 50 times their weight of water. Suitable superabsorbent particulate material can be prepared from carboxymethylcellulose and its sodium and potassium salts, hydroxymethylcellulose, hydroxyethylcellulose, poly(acrylamide), poly(acrylic acid) and its sodium and potassium salts, alginates, and starch-graft copolymers such as those of acrylates and acrylamides and their salts. Examples of such materials are disclosed in U.S. Pat. No. 5,064,653 (Sessions et al.). Although superabsorbent particles are preferred, other absorbent particles can be used if desired, such as gelatins, polysaccharides, gums including pectin, guar gum, xantham gum, and karaya gum.

Examples of other additives that can be included into the backing and/or adhesive include odor absorbers such as activated carbon, medicaments such as chlorhexidine gluconate, biologically active agents, cosmetic agents, and the like, which can be in particulate form or incorporated into encapsulating agents.

The adhesive and/or backing can also include dye-based or pigment-based inks in the form of an image (e.g., text or picture). Preferably, the adhesive layer includes an image that becomes visible upon removal and delamination. The image can be applied using a wide variety of conventional techniques, such as ink jet printing, electrophotography, screen printing, etc.

EXAMPLES

The objects, features, and advantages of the present invention illustrated in the following examples, which incorporate particular materials and amounts, should not be construed to unduly limit this invention. All materials are commercially available unless otherwise stated or apparent. All parts, percentages, ratios, etc., in the examples are by weight unless otherwise indicated.

Glossary

| Adhesives | |
|---|---|
| Adhesive A | Fibers-containing polyacrylate pressure sensitive adhesive (PSA) (5-mil (0.13-mm) thick) prepared as described in Example 20 of Applicants' Assignee's copending U.S. patent application Ser. No. 09/764,478, entitled "Pressure Sensitive Adhesives and a Fibrous Reinforcing Material," filed on 17 Jan. 2001. |
| Adhesive B | Tackified KRATON PSA comprising 50 weight % KRATON 1107 (a styrene-isoprene copolymer thermoplastic elastomer, Shell Chemical Co., Houston, TX) and 50 weight % ESCOREZ 1310 tackifier (an aliphatic resin, Exxon Chemical Co., Houston, TX); hot-melt coated at an 8-mil (0.2-mm) thickness on a standard release liner. |
| Adhesive C | A PSA blend (75/25) of an isooctyl acrylate/acrylic acid PSA and KRATON D1107P (styrene-isoprene-styrene block copolymer) prepared as described in Example 1 of International Publication No. WO 96/25469 (Hyde et al.). The PSA was extruded to a thickness of 0.12 mm. |
| Adhesive D | A multi-layer co-extruded PSA material made from 61 layers of alternating ABABA . . . (where A is an acrylic PSA and B is a hydrophilic polyurethane) as described in Example 11 of U.S. Pat. No. 6,045,895 (Hyde et al.). Two 0.06-mm thick extruded layers of this PSA material were laminated together to provide Adhesive D (0.12-mm thick). |
| Adhesive E | A multi-layer co-extruded PSA material made from 61 layers of alternating ABABA . . . (where A is an acrylic PSA and B is a polyether-block-amide) as described in Example 12 of U.S. Pat. No. 6,045,895 (Hyde et al.). Two 0.06-mm thick extruded layers of this PSA material were laminated together to provide Adhesive B (0.12-mm thick). |
| Adhesive F | Fiber-containing polyacrylate pressure sensitive adhesive prepared as described in Example 28 of Applicants' Assignee's copending U.S. patent application Ser. No. 09/764,478, entitled "Pressure Sensitive Adhesives and a Fibrouse Reinforcing Material," filed on 17 Jan. 2001. |
| Backings | |
| Polyurethane | Melt-blown nonwoven fibrous web comprised of three-layer polymeric fibers having a center layer of blended polyethylene and KRATON PSA, and outer layers of polyurethane; prepared as described for Backing Sample 16 in U.S. Pat. No. 6,107,219 (Joseph et al.); typically represents an elastic, non-tearable backing. |
| Paper | Hammermill Laserprint paper (0.11-mm thick), Product No. 00460-4, International Paper, Memphis, TN); typically represents a non-stretchable, tearable backing. |
| Polyethylene | Melt-blown nonwoven polyethylene (0.04-mm thick, Style No. TM07-27-98-02, Trans Web LLC, Vineland, NJ); typically represents a stretchable, tearable backing. |
| Polypropylene | Melt-blown nonwoven polypropylene (basis weight 20 g/m$^2$, Kimberly-Clark, Irving, TX); typically represents a non-stretchable, tearable backing. |
| Film | Polymer film comprising 60% ethylene/vinyl acetate copolymer, 35% linear low density polyethylene, 5% stabilizers and other additives (PGI Product No. 6012, Polymer Group, Inc., Gainesville, GA); film had a basis weight of 1.15 oz/yd$^2$ (27 g/m$^2$), was 5-mils (0.13-mm) thick, and had oval-shaped holes (approximately 0.2-mm width × 0.3-mm length in the greatest dimensions) with the length dimension of the oval holes oriented parallel to the machine direction of the film. The film had about 530 holes/cm$^2$ arranged in a pattern of staggered lines. One side of the film was "smooth" (microetched/embossed for smoothness) and the other side was "rough" (side that had material pushed out from forming the holes). |

Test protocols

Tape Removal Method

A tape sample having a laminated backing/adhesive construction was adhered with thumb pressure onto a mirror-finished steel plate with about 1-cm length of the sample extending over the end of the plate. The over-extending portion of the sample was finger-grasped and stretched in the plane of the adhesive-backing interface at a rate of about 152 cm/min. Upon stretching, the adhesive released from the plate surface. The tape construction was visually checked to determine, over the area of the sample that was removed from the steel plate by stretching, whether at least 50% of the area of the backing was separated from the adhesive during stretch removal. In these examples, the tape sample was considered to have delaminated if at least 50% of the backing layer area had separated from the adhesive layer. (The area of the backing can change during the stretch removal process; the new area of the backing was considered in determining whether delamination had occurred to an extent of at least 50%.)

Examples 1A–6C and Comparative Example 1

Stretch Removable First Aid Dressings

First Aid Dressing (FAD) materials were made by laminating an 8.5-cm×12.5-cm sheet of backing to an 8.5-cm× 12.5-cm sheet of adhesive. In all cases, the adhesive and backing were laminated using a Carver Laboratory Press, Model C (Fred Carver Inc., Subsidiary of Sterling, Inc., Menomonee Falls, Wis.) with a 1000-lb (4450-N) force for 5 seconds at room temperature (approximately 23° C.), 70° C., or 100° C. The various FAD constructions (Examples 1A to 6C), including the specific backings and adhesives used (see Glossary), are provided in Table 1.

It was noted that the Polyurethane and Polyethylene nonwoven backings were both rougher on one side than the other due to the collection technique used during the melt-blown process. (For example, a nonwoven web collected on a smooth collector will be "smooth" on the side facing the collector and "rough" on the side facing the die.) For each of the Examples presented in Table 1 (1A–C, 2A–C, 5A–C, and 6A–C), FAD samples were made with the adhesive laminated to both the "rough" and the "smooth" sides of the backings. No differences in evaluation results were attributed to whether the adhesive was laminated to "rough" or "smooth" sides of the backing.

In the case of the FAD constructions that contained the polyacrylate Adhesive A (Examples 1A–C, 3A–C, and 5A–C), the adhesive sheet was laminated to the backing in such a way that the FAD, when stretched for removal, was stretched parallel to the machine direction of the adhesive sheet.

In the case of Examples 1A–C and 2A–C, the Polyurethane backing was broken prior to lamination.

Comparative Example 1 (CE-1) was prepared by hot-melt coating the KRATON Adhesive B onto the Polyurethane backing at a thickness of 0.2 mm.

TABLE 1

Laminated Stretch Removable First Aid Dressings

| Ex. | Lamin. Temp. ° C. | Backing Layer | Adhesive Layer | Delamination on Removal |
|---|---|---|---|---|
| 1A | 23 | Polyurethane | Adhesive A | Yes |
| 1B | 70 | Polyurethane | Adhesive A | Yes (Adhesive Layer Broke) |
| 1C | 100 | Polyurethane | Adhesive A | No |
| 2A | 23 | Polyurethane | Adhesive B | Yes |

TABLE 1-continued

Laminated Stretch Removable First Aid Dressings

| Ex. | Lamin. Temp. °C. | Backing Layer | Adhesive Layer | Delamination on Removal |
|---|---|---|---|---|
| 2B | 70 | Polyurethane | Adhesive B | No (Adhesive Layer Stretched w/ Backing) |
| 2C | 100 | Polyurethane | Adhesive B | No |
| 3A | 23 | Paper | Adhesive A | Yes |
| 3B | 70 | Paper | Adhesive A | Yes |
| 3C | 100 | Paper | Adhesive A | Yes (Adhesive Layer Broke) |
| 4A | 23 | Paper | Adhesive B | Yes |
| 4B | 70 | Paper | Adhesive B | Yes (Adhesive Layer Broke) |
| 4C | 100 | Paper | Adhesive B | No |
| 5A | 23 | Polyethylene | Adhesive A | Yes |
| 5B | 70 | Polyethylene | Adhesive A | Yes |
| 5C | 100 | Polyethylene | Adhesive A | No |
| 6A | 23 | Polyethylene | Adhesive B | Yes |
| 6B | 70 | Polyethylene | Adhesive B | Yes |
| 6C | 100 | Polyethylene | Adhesive B | No |
| CE-1 | NA* | Polyurethane | Adhesive B | No |

*Not Applicable; KRATON Adhesive B hot-melt coated onto the Polyurethane backing.

The laminated FAD materials were cut into 1.2-cm×4.0-cm tape samples and evaluated for delamination during removal by stretching from a steel plate according to the Tape Removal Method described herein. Whether or not the FAD samples delaminated upon stretch and removal from the plate is indicated in Table 1.

In the case of Examples 1A–C and 2A–C that were constructed with a Polyurethane backing, the backing layer of the tape samples was cut at each end so that the adhesive layer, together with a portion of the backing that was cut, could be stretched. For all other Examples (3A–6C), the backing broke during stretching at least at the position extending over the end of the steel plate.

All of the tape samples that had been laminated at 23° C. (1A, 2A, 3A, 4A, 5A, and 6A) were observed to delaminate when stretched and removed from the steel plate; all but one of the samples that had been laminated at 70° C. (1B, 3B, 4B, 5B, and 6B) were observed to delaminate when stretched and removed; and only one of the samples that had been laminated at 100° C. (3C) was observed to delaminate when stretched and removed. The Comparative Example (CE-1) tape sample did not delaminate when stretched and removed from the steel plate.

Examples 7A–B

Stretch Removable First Aid Dressings

A FAD sample was made by laminating with thumb pressure at room temperature a strip (0.6-cm×5.1-cm) of the perforated polymer Film backing (see Glossary) to a strip (0.6-cm×5.1-cm) of the KRATON Adhesive B with the "smooth" side of the Film backing against the adhesive (Example 7A). Another FAD sample was made in the same manner, except with the "rough" side of the Film backing against the adhesive (Example 7B).

The laminated FAD samples were evaluated for delamination during removal by stretching from a steel plate according to the Tape Removal Method described herein. The Example 7B sample was observed to delaminate when stretched and removed from the steel plate, but there was no evidence of delamination when the Example 7A sample was stretched and removed.

Example 8

Stretch Removable First Aid Dressing

The Polyurethane backing (see Glossary) was perforated with a metal die to provide parallel rows of holes separated by 3.8 cm. The holes were rectangular in shape (1.75-mm× 0.07-mm) and the space between holes within a row was 0.7 mm. The Polyurethane backing had one side rougher than the other due to the collection technique used during the melt-blown process.

A FAD sample was made by laminating with thumb pressure at room temperature a strip (2.54-cm×7.6-cm) of the perforated Polyurethane backing to a strip (2.54-cm× 7.6-cm) of the KRATON Adhesive B with the "rough" side of the backing against the adhesive and with the rows of holes perpendicular to the long axis of the sample. A 1.8-cm×2.5-cm gauze pad was attached to the adhesive layer in the center of the sample and the holes had been pre-cut such that the rows began 6 mm from each end of the sample.

The FAD sample was evaluated for delamination during removal by adhering the sample with finger pressure to the forearm of a human subject, waiting 10 minutes, and then removing by lifting and stretching the gauze pad at about a 90° angle to the plane of the forearm. Very little force was required to stretch the backing and to remove the sample painlessly from the skin and hair of the forearm. During stretching and removal, the backing was observed to break and to delaminate from the adhesive layer.

Example 9

Stretch Removable First Aid Dressing

The Paper backing (see Glossary) was perforated with a metal die to provide parallel rows of holes separated by 6.35 cm. The holes were rectangular in shape (1.75-mm×0.07-mm) with the long sides of the holes oriented in the direction of the rows and the space between holes within a row was 0.7 mm.

A FAD sample was made by laminating with thumb pressure at room temperature a strip (2.54-cm×7.6-cm) of the perforated Paper backing to a strip (2.54-cm×7.6-cm) of the Polyacrylate Adhesive A with fibrils of the adhesive and the rows of holes perpendicular to the long axis of the sample. A 1.8-cm×2.5-cm gauze pad was attached to the adhesive layer in the center of the sample and the holes had been pre-cut such that the rows began 6 mm from each end of the sample.

The FAD sample was evaluated for delamination during removal by adhering the sample with finger pressure to the forearm of a human subject, waiting 10 minutes, and then removing by pulling one end of the sample and stretching the sample at about a 35° angle to the plane of the forearm. Very little force was required to stretch the backing and to remove the sample painlessly from the skin and hair of the forearm. During stretching and removal, the backing was observed to break and to delaminate from the adhesive layer.

Examples 10A–B

Stretch Removable First Aid Dressings

FAD sample was made as described in Example 1A by laminating at room temperature a sheet of the Polyurethane backing to a sheet of Adhesive C with the "rough" side of the backing against the adhesive (Example 10A). Another FAD sample was prepared in the same manner except that the "smooth" side of the backing was against the adhesive (Example 10B). For both Examples 10A and 10B, the Polyurethane backing was perforated before lamination as described for the Paper backing in Example 9.

The laminated FAD samples were evaluated for delamination during removal by stretching from a steel plate according to the Tape Removal Method described herein. Both Examples 10A and 10B samples were observed to delaminate when stretched and removed from the steel plate The FAD samples were also evaluated for delamination during removal by adhering each sample with finger pressure to the forearm of a human subject, waiting 10 minutes, and then removing by pulling one end of the sample and stretching the sample at about a 35° angle to the plane of the forearm. For both Examples 10A and 10B, very little force was required to stretch the backing and to remove the sample painlessly from the skin and hair of the forearm. During stretching and removal, the backing was observed to break and to delaminate from the adhesive layer.

Example 11

Stretch Removable First Aid Dressing

A FAD sample was made as described in Example 10A, except that Adhesive D was used in place of Adhesive C. The sample was evaluated and the same results obtained as described in Example 10A.

Example 12

Stretch Removable First Aid Dressing

A FAD sample was made as described in Example 10A, except that Adhesive E was used in place of Adhesive C. The sample was evaluated and the same results obtained as described in Example 10A.

Example 13

Stretch Removable First Aid Dressing

A FAD sample was made by laminating with thumb pressure at room temperature a strip (2.54-cm×7.6-cm) of the Polypropylene backing (see Glossary) to a strip (2.54-cm×7.6-cm) of the Adhesive A. A 1.3-cm piece of the adhesive/backing laminate was gathered in the middle of the strip in such a way that a fold was made perpendicular to the greatest length of the strip. A 1.8-cm×2.5-cm gauze pad was attached to the adhesive layer in the center of the sample.

The FAD sample was evaluated for delamination during removal by adhering the sample with finger pressure to the forearm of a human subject, waiting 10 minutes, and then using the fold in the FAD as a handle, removing by lifting and stretching the gauze pad at about a 90° angle to the plane of the forearm. Very little force was required to stretch the backing and to remove the sample painlessly from the skin and hair of the forearm. During stretching and removal, the backing was observed to break and to delaminate from the adhesive layer.

Example 14

Stretch Removable First Aid Dressing

A FAD sample having a center fold and a gauze pad was made as described in Example 13, except that the Polyurethane backing (see Glossary) was used in place of the Polypropylene backing. The sample was evaluated as described in Example 13. During stretching and removal, the backing was observed to delaminate from the adhesive layer.

Example 15

Stretch Removable First Aid Dressing

A FAD sample having a center fold and a gauze pad was made as described in Example 13, except that Adhesive F was used in place of Adhesive A. The sample was evaluated and the same results obtained as described in Example 13.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A method of removing a medical article from skin, the method comprising:
   providing a medical article adhered to skin, wherein the medical article comprises a backing and a stretch removable pressure sensitive adhesive layer disposed thereon; and
   stretching the medical article in an amount sufficient to delaminate the adhesive layer from the backing and remove the medical article from the skin.

2. The method of claim 1 wherein stretching the medical article comprises stretching it in a direction substantially parallel to the plane of the skin to which it is adhered.

3. The method of claim 1 wherein the backing and the adhesive layer are selected such that the stretchability of the adhesive layer is greater than that of the backing under the same tension.

4. The method of claim 3 wherein the stretchability at break of the adhesive layer is at least about 300%.

5. The method of claim 4 wherein the stretchability at break of the adhesive layer is no greater than about 800%.

6. The method of claim 3 wherein the stretchability at break of the adhesive layer is at least about 10% greater than that of the backing.

7. The method of claim 1 wherein the adhesive layer comprises a poly(meth)acrylate.

8. The method of claim 1 wherein the adhesive layer comprises a reinforced adhesive.

9. The method of claim 8 wherein the adhesive layer comprises a fibrous reinforcing material.

10. The method of claim 9 wherein the adhesive layer comprises:
    a pressure sensitive adhesive matrix; and
    a fibrous reinforcing material within the pressure sensitive adhesive matrix;
    wherein the adhesive layer has a yield strength and a tensile strength, and wherein the tensile strength is about 0.7 MPa or greater, and at least about 150% of the yield strength.

11. The method of claim 10 wherein the pressure sensitive adhesive matrix comprises a polymer derived from at least one alkyl ester monomer selected from isooctyl acrylate, 2-ethyl-hexyl acrylate, and n-butyl acrylate, and at least one co-monomer selected from acrylic acid and acrylamide.

12. The method of claim 1 wherein the adhesive layer comprises an A-B-A block copolymer.

13. The method of claim 1 wherein the medical article is in the form of a wound dressing, surgical dressing, medical tape, athletic tape, or surgical drape.

14. The method of claim 1 wherein the medical article is in the form of a sensor, an electrode, or an ostomy appliance.

15. A method of removing a medical article from skin, the method comprising:
providing a medical article adhered to skin, wherein the medical article comprises a backing and a stretch removable pressure sensitive adhesive layer disposed thereon;
wherein the backing and the adhesive layer are selected such that the stretchability of the adhesive layer is greater than that of the backing under the same tension;
wherein the stretch removable pressure sensitive adhesive layer comprises:
a pressure sensitive adhesive matrix; and
a fibrous reinforcing material within the pressure sensitive adhesive matrix;
and further wherein the adhesive layer has a yield strength and a tensile strength, and wherein the tensile strength is about 0.7 MPa or greater, and at least about 150% of the yield strength; and
stretching the medical article in an amount sufficient to delaminate the adhesive layer from the backing and remove the medical article from the skin.

16. A method of removing a medical article from skin, the method comprising:
providing a medical article adhered to skin, wherein the medical article comprises a backing and a stretch removable pressure sensitive adhesive layer disposed thereon;
wherein the backing and the adhesive layer are selected such that the stretchability of the adhesive layer is greater than that of the backing under the same tension;
wherein the stretch removable pressure sensitive adhesive layer comprises:
a pressure sensitive adhesive matrix comprising a polymer derived from at least one alkyl ester monomer selected from isooctyl acrylate, 2-ethyl-hexyl acrylate, and n-butyl acrylate; and at least one co-monomer selected from acrylic acid and acrylamide; and
a fibrous reinforcing material within the pressure sensitive adhesive matrix;
and further wherein the adhesive layer has a yield strength and a tensile strength, and wherein the tensile strength is about 0.7 MPa or greater, and at least about 150% of the yield strength; and
stretching the medical article in a direction relative to the skin to which it is adhered sufficient to delaminate the adhesive layer from the backing and remove the medical article from the skin.

17. A medical article comprising a backing and a stretch removable pressure sensitive adhesive layer disposed thereon, wherein the backing and the adhesive layer are selected such that the stretchability of the adhesive layer is greater than that of the backing under the same tension and the adhesive layer and backing delaminate when removed from skin.

18. The medical article of claim 17 wherein the adhesive layer comprises an A-B-A block copolymer.

19. The medical article of claim 17 wherein the backing comprises melt blown fibers.

20. The medical article of claim 17 which is in the form of a wound dressing, surgical dressing, medical tape, athletic tape, or surgical drape.

21. The medical article of claim 17 which is in the form of a sensor, an electrode, or an ostomy appliance.

22. The medical article of claim 17 wherein the stretchability at break of the adhesive layer is at least about 300%.

23. The medical article of claim 17 wherein the stretchability at break of the adhesive layer is at least about 10% greater than that of the backing.

24. The medical article of claim 17 wherein the adhesive layer and backing form separate phases.

25. The medical article of claim 17 wherein the adhesive layer comprises a poly(meth)acrylate.

26. The medical article of claim 17 wherein the adhesive layer comprises a fibrous reinforcing material.

27. The medical article of claim 26 wherein the adhesive layer comprises:
a pressure sensitive adhesive matrix; and
a fibrous reinforcing material within the pressure sensitive adhesive matrix;
wherein the adhesive layer has a yield strength and a tensile strength, and wherein the tensile strength is about 0.7 MPa or greater, and at least about 150% of the yield strength.

28. The medical article of claim 27 wherein the pressure sensitive adhesive matrix comprises a polymer derived from at least one alkyl ester monomer selected from isooctyl acrylate, 2-ethyl-hexyl acrylate, and n-butyl acrylate, and at least one co-monomer selected from acrylic acid and acrylamide.

29. A method of making a medical article, the method comprising:
providing a backing;
selecting a stretch removable pressure sensitive adhesive layer such that the stretchability of the adhesive layer disposed on the backing is greater than that of the backing under the same tension; and
laminating the backing and the pressure sensitive adhesive layer together under conditions of temperature and pressure that allow the adhesive layer and backing to delaminate when removed from skin.

30. A stretch removable adhesive article comprising a backing with a predefined tab and a pressure sensitive adhesive layer disposed on a major surface of the backing opposite that of the tab, wherein the predefined tab is located in a central portion of the backing.

31. The article of claim 30 wherein the pressure sensitive adhesive is a stretch removable pressure sensitive adhesive.

32. The article of claim 30 wherein the backing and the adhesive layer are selected such that the stretchability of the adhesive layer is greater than that of the backing under the same tension.

33. The article of claim 32 wherein the stretchability at break of the adhesive layer is at least about 300%.

34. The article of claim 32 wherein the stretchability at break of the adhesive layer is no greater than about 800%.

35. The article of claim 32 wherein the stretchability at break of the adhesive layer is at least about 10% greater than that of the backing.

36. The article of claim 30 wherein the adhesive layer comprises a poly(meth)acrylate.

37. The article of claim 30 wherein the adhesive layer comprises a reinforced adhesive.

38. The article of claim 37 wherein the adhesive layer comprises a fibrous reinforcing material.

39. The article of claim 38 wherein the adhesive layer comprises:

a pressure sensitive adhesive matrix; and a fibrous reinforcing material within the pressure sensitive adhesive matrix;

wherein the adhesive layer has a yield strength and a tensile strength, and wherein the tensile strength is about 0.7 MPa or greater, and at least about 150% of the yield strength.

40. The article of claim 39 wherein the pressure sensitive adhesive matrix comprises a polymer derived from at least one alkyl ester monomer selected from isooctyl acrylate, 2-ethyl-hexyl acrylate, and n-butyl acrylate, and at least one co-monomer selected from acrylic acid and acrylamide.

41. The article of claim 30 wherein the adhesive layer comprises an A-B-A block copolymer.

42. The article of claim 30 wherein the tab comprises a portion of the backing and portion of the adhesive layer.

43. The article of claim 30 wherein the backing comprises two pieces.

44. The article of claim 43 wherein the two backing pieces overlap.

45. The article of claim 43 wherein each backing piece comprises an end free of exposed adhesive, and further wherein the ends free of exposed adhesive form the predefined tabs.

46. The article of claim 30 which is a medical article.

47. The article of claim 46 which is in the form of a wound dressing, surgical dressing, medical tape, athletic tape, or surgical drape.

48. The article of claim 46 which is in the form of a sensor, an electrode, or an ostomy appliance.

49. A stretch removable adhesive article comprising a backing with a predefined tab and a stretch removable pressure sensitive adhesive layer disposed thereon, wherein the predefined tab is located in a central portion of the backing, and further wherein the backing and the adhesive layer are selected such that the stretchability of the adhesive layer is greater than that of the backing under the same tension.

50. A stretch removable adhesive article comprising a backing with a predefined tab and a stretch removable pressure sensitive adhesive layer disposed thereon, wherein:

the predefined tab is located in a central portion of the backing;

the backing and the adhesive layer are selected such that the stretchability of the adhesive layer is greater than that of the backing under the same tension; and the adhesive layer comprises:

a pressure sensitive adhesive matrix; and a fibrous reinforcing material within the pressure sensitive adhesive matrix;

wherein the adhesive layer has a yield strength and a tensile strength, and wherein the tensile strength is about 0.7 MPa or greater, and at least about 150% of the yield strength.

51. A method of removing an article from a surface, the method comprising:

providing a stretch removable adhesive article adhered to a surface, wherein the article comprises a backing with a predefined tab and a pressure sensitive adhesive layer disposed thereon, wherein the predefined tab is located in a central portion of the backing; and pulling on the tab to stretch the adhesive article in an amount sufficient to remove the article from the surface.

52. The method of claim 51 wherein the pressure sensitive adhesive is a stretch removable pressure sensitive adhesive.

53. The method of claim 51 wherein the backing and the adhesive layer are selected such that the stretchability of the adhesive layer is greater than that of the backing under the same tension.

54. The method of claim 53 wherein the stretchability at break of the adhesive layer is at least about 300%.

55. The method of claim 53 wherein the stretchability at break of the adhesive layer is at least about 10% greater than that of the backing.

56. The method of claim 51 wherein the adhesive layer comprises a poly(meth)acrylate.

57. The method of claim 51 wherein the adhesive layer comprises a reinforced adhesive.

58. The method of claim 57 wherein the adhesive layer comprises:

a pressure sensitive adhesive matrix; and a fibrous reinforcing material within the pressure sensitive adhesive matrix;

wherein the adhesive layer has a yield strength and a tensile strength, and wherein the tensile strength is about 0.7 MPa or greater, and at least about 150% of the yield strength.

59. The method of claim 58 wherein the pressure sensitive adhesive matrix comprises a polymer derived from at least one alkyl ester monomer selected from isooctyl acrylate, 2-ethyl-hexyl acrylate, and n-butyl acrylate, and at least one co-monomer selected from acrylic acid and acrylamide.

60. The method of claim 51 wherein the adhesive layer comprises an A-B-A block copolymer.

61. The method of claim 51 wherein the tab comprises a portion of the backing and portion of the adhesive layer.

62. The method of claim 51 wherein the backing comprises two pieces.

63. The method of claim 62 wherein the two backing pieces overlap.

64. The method of claim 62 wherein each backing piece comprises an end free of exposed adhesive, and further wherein the ends free of exposed adhesive form the predefined tabs.

65. The method of claim 51 wherein the article is a medical article.

66. The method of claim 65 wherein the medical article is in the form of a wound dressing, surgical dressing, medical tape, athletic tape, or surgical drape.

67. The method of claim 65 wherein the medical article is in the form of a sensor, an electrode, or an ostomy appliance.

68. A method of making a medical article, the method comprising:

providing a backing with a predefined tab located in a central portion of the backing; and applying a stretch removable pressure sensitive adhesive to a major surface of the backing opposite that of the predefined tab.

69. A method of removing an article from a surface, the method comprising:

providing a stretch removable adhesive article adhered to a surface, wherein the article comprises a backing with a predefined tab and a pressure sensitive adhesive layer disposed thereon, wherein the predefined tab is located in a central portion of the backing; and pulling on the tab along a direction that is normal to the surface to stretch the adhesive article in an amount sufficient to remove the article from the surface.

70. A method of removing an article from a surface, the method comprising:

providing a stretch removable adhesive article adhered to a surface, wherein the article comprises a backing and a pressure sensitive adhesive layer disposed thereon;

rotating a portion of the article to a nearly perpendicular orientation from its starting position; and pulling on the rotated portion of the article along a direction that is not normal to the surface to stretch the adhesive article in an amount sufficient to remove the article from the surface.

71. The method of claim 70 wherein the direction forms an angle of about 20 degrees or more off of normal.

72. The method of claim 70 wherein the backing comprises a predefined tab and pulling on the rotated portion of the article comprises pulling on the predefined tab.

73. The method of claim 72 wherein the predefined tab is located in a central portion of the backing.

74. The method of claim 70 wherein the article is a wound dressing.

75. The method of claim 70 wherein the surface is skin.

76. A method of removing an article from a surface, the method comprising;

providing a stretch removable adhesive article adhered to a surface, wherein the article has a center axis and comprises a backing having a plane and a pressure sensitive adhesive layer disposed on the backing;

grasping an edge portion at the center of the article so that the plane of the backing stays substantially parallel to the plane of the surface; and pulling on the edge portion of the article along a direction that is substantially perpendicular to the center axis of the article and along the plane of the surface to stretch the article in an amount sufficient to remove the article from the surface.

77. The method of claim 76 wherein the article is a wound dressing.

78. The method of claim 76 wherein the surface is skin.

* * * * *

UNITED STATES PATENT AND TRADEMARK OFFICE
CERTIFICATE OF CORRECTION

| | |
|---|---|
| PATENT NO. | : 7,078,582 B2 |
| APPLICATION NO. | : 09/934450 |
| DATED | : July 18, 2006 |
| INVENTOR(S) | : William L. Stebbings |

It is certified that error appears in the above-identified patent and that said Letters Patent is hereby corrected as shown below:

<u>First Page Item (56)</u>
Column 2, Line 2, under "Other Publications", delete "Test,"" and insert -- Test)," --, therefor.

<u>Page 2 Item (56)</u>
Column 1, Line 61, under "US Patent Documents", delete "L ühmann" and insert -- Lühmann -- therefor.

Item (56)
Column 2, Line 25, under "Foreign Patent Documents", below "TW 267938" insert -- TW 376748 --.

Column 2, Line 50, under "Foreign Patent Documents "below "WO  WO 02/089719 Al 11/2002" insert -- OTHER PUBLICATIONS --.(As a heading)

Column 2, line 8, under "Other Publications", after "Tapes" insert -- at --.

<u>Column 21</u>
Line 33, after "Adhesive" delete "B" and insert -- E --, therefor.
Line 38, delete "Fibrouse" and insert -- Fibrous --, therefor.

<u>Column 22</u>
Line 16, delete "50%.)" and insert --50%).--, therefor.

<u>Column 25</u>
Line 9, after "plate" insert -- . --.

UNITED STATES PATENT AND TRADEMARK OFFICE
CERTIFICATE OF CORRECTION

PATENT NO. : 7,078,582 B2 Page 2 of 2
APPLICATION NO. : 09/934450
DATED : July 18, 2006
INVENTOR(S) : William L. Stebbings It is certified that error appears in the above-identified patent and that said Letters Patent is hereby corrected as shown below:

<u>Column 32</u>
Line 2, In Claim 76, delete "comprising;" and insert -- comprising: --, therefor.

Signed and Sealed this

Fifteenth Day of May, 2007

JON W. DUDAS
*Director of the United States Patent and Trademark Office*